(12) United States Patent
Tang et al.

(10) Patent No.: US 12,247,220 B2
(45) Date of Patent: Mar. 11, 2025

(54) 3D PRINTED MICRO-MILLIFLUIDIC BIOREACTORS FOR LONG-TERM RETINAL ORGANOID MAINTENANCE

(71) Applicant: The Regents of the University of California, Oakland, CA (US)

(72) Inventors: William C. Tang, Irvine, CA (US); Andrew W. Browne, Newport Coast, CA (US); Magdalene J. Seiler, Orange, CA (US); Yuntian Xue, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/903,458

(22) Filed: Sep. 6, 2022

(65) Prior Publication Data

US 2023/0077412 A1   Mar. 16, 2023

Related U.S. Application Data

(60) Provisional application No. 63/241,142, filed on Sep. 7, 2021.

(51) Int. Cl.
*C12N 5/079* (2010.01)
*C12M 1/00* (2006.01)
(Continued)

(52) U.S. Cl.
CPC ......... *C12N 5/0621* (2013.01); *C12M 1/3476* (2013.01); *C12M 23/16* (2013.01);
(Continued)

(58) Field of Classification Search
CPC ................. C12N 5/0621; C12N 5/062; C12N 2501/115; C12N 2501/16; C12N 2501/91;
(Continued)

(56) References Cited

U.S. PATENT DOCUMENTS

| | | | | |
|---|---|---|---|---|
| 2004/0132166 A1* | 7/2004 | Miller | ............... | B01L 3/502707 435/286.1 |
| 2010/0071486 A1* | 3/2010 | Kim | .................. | B01L 3/502753 73/864.81 |
| 2020/0318045 A1* | 10/2020 | Jackson-Holmes | .... | C12M 23/16 |

OTHER PUBLICATIONS

C.-C. Hong, et al., A novel in-plane passive microfluidic mixer with modified Tesla structures, Lab on a Chip, 2004, 4, 109-113.
(Continued)

*Primary Examiner* — Michael L Hobbs
(74) *Attorney, Agent, or Firm* — Brooks Kushman P.C.

(57) ABSTRACT

A bioreactor device includes a solid substrate having a first face and a second face. The solid substrate at least partially defines a perfusion channel, a plurality of chambers, a fluidic inlet, and a fluidic outlet. A first sheet disposed over the first face and a second sheet disposed over the second face. Characteristically, the combination of the solid substrate, the first sheet and the second sheet define the perfusion channel and each chamber of the plurality of chambers. The plurality of chambers are arranged in rows of chambers in which adjacent chambers are positioned at opposite side of the perfusion channel. The perfusion channel extends from the fluidic inlet and the fluidic outlet having a serpentine path along each row of chambers with each chamber being in fluid communication with the perfusion channel.

15 Claims, 31 Drawing Sheets
(19 of 31 Drawing Sheet(s) Filed in Color)

(51) Int. Cl.
C12M 1/06 (2006.01)
C12M 1/34 (2006.01)
C12M 3/06 (2006.01)
C12N 5/0793 (2010.01)

(52) U.S. Cl.
CPC ............ *C12M 23/22* (2013.01); *C12M 27/02* (2013.01); *C12M 29/10* (2013.01); *C12N 5/062* (2013.01)

(58) Field of Classification Search
CPC ............ C12N 2506/00; C12N 2510/00; C12N 2513/00; C12N 2533/90; C12M 1/3476; C12M 23/16; C12M 23/22; C12M 23/12; C12M 27/02; C12M 29/10; C12M 41/36; B33Y 80/00
See application file for complete search history.

(56) References Cited

OTHER PUBLICATIONS

A. Sridhar, et al., Single-Cell Transcriptomic Comparison of Human Fetal Retina, hPSC-Derived Retinal Organoids, and Long-Term Retinal Cultures, Cell reports, 2020, 30, 1644-1659. e1644.

K. Shekhar, et al., Comprehensive Classification of Retinal Bipolar Neurons by Single-Cell Transcriptomics, Cell, 2016, 166, 1308-1323. e1330.

J. E. Niven, et al., Energy limitation as a selective pressure on the evolution of sensory systems, The Journal of experimental biology, 2008, 211, 1792-1804.

R. P. Wolfe, et al., Shear Stress During Early Embryonic Stem Cell Differentiation Promotes Hematopoietic and Endothelial Phenotypes, Biotechnology and bioengineering, 2013, 110, 1231-1242.

S. Regmi, et al., High Shear Stresses under Exercise Condition Destroy Circulating Tumor Cells in a Microfluidic System, Scientific Reports, 2017, 7, 39975.

J. A. Frangos, et al., Shear Stress Induced Stimulation of Mammalian Cell Metabolism, Biotechnology and bioengineering, 1988, 32, 1053-1060.

P. Ovando-Roche, et al., Use of bioreactors for culturing human retinal organoids improves photoreceptor yields, Stem Cell Research & Therapy, 2018, 9, 156.

A. Schwartz, Chronic Open-Angle Glaucoma Secondary to Rhegmatogenous Retinal Detachment, Transactions of the American Ophthalmological Society, 1972, 70, 178.

Y. C. Smith, et al., Novel Three-Dimensional Organoid Model for Evaluation of the Interaction of Uropathogenic *Escherichia coli* with Terminally Differentiated Human Urothelial Cells, A. D., 2006.

A. J. Carterson, et al., A549 Lung Epithelial Cells Grown as Three-Dimensional Aggregates: Alternative Tissue Culture Model for Pseudomonas aeruginosa Pathogenesis, Infection and Immunity, 2005, 73, 1129-1140.

R. Salerno-Goncalves, et al., Development of a Multicellular Three-dimensional Organotypic Model of the Human Intestinal Mucosa Grown Under Microgravity, J Vis Exp, 2016, DOI: 10.3791/54148.

B. E. Hjelm, et al., Development and Characterization of a Three-Dimensional Organotypic Human Vaginal Epithelial Cell Model, Biol Reprod, 2010, 82, 617-627.

K. A. Homan, et al., Flow-enhanced vascularization and maturation of kidney organoids in vitro, Nat Methods, 2019, 16, 255-262.

S. D. Ramachandran, et al., In Vitro Generation of Functional Liver Organoid-Like Structures Using Adult Human Cells, PLoS One, 2015, 10, e0139345.

M. Kasendra, et al., Development of a primary human Small Intestine-on-a-Chip using biopsy-derived organoids, Sci Rep, 2018, 8, 2871.

Y. S. Zhang, et al., Multisensor-integrated organs-on-chips platform for automated and continual in situ monitoring of organoid behaviors, Proc Natl Acad Sci U S A, 2017, 114, E2293-E2302.

G. Mattei, et al., Design Criteria for Generating Physiologically Relevant In Vitro Models in Bioreactors, Arti, 2014, 2, 548-569.

N. P. Macdonald, et al., Comparing Microfluidic Performance of Three-Dimensional (3D) Printing Platforms, Analytical Chemistry, 2017, 89, 3858-3866.

K. P. Archberger, et al., Merging organoid and organ-on-a-chip technology to generate complex multi-layer tissue models in a human retina-on-a-chip platform, eLife 2019, DOI: 10.7554/eLife.46188.

A. W. Browne, , Structural and Functional Characterization of Human Stem-Cell-Derived Retinal Organoids by Live Imaging, Invest Ophthalmol Vis Sci, 2017, 58, 3311-3318.

C. Stringari, et al., Metabolic trajectory of cellular differentiation in small intestine by Phasor Fluorescence Lifetime Microscopy of NADH, Scientific reports, 2012, 2, 1-9.

B. K. Wright, et al., NADH Distribution in Live Progenitor Stem Cells by Phasor-Fluorescence Lifetime Image Microscopy, Biophysical journal, 2012, 103, L7-L9.

R. Datta, et al., Label-free imaging of metabolism and oxidative stress in human induced pluripotent stem cell-derived cardiomyocytes, Biomedical optics express, 2016, 7, 1690-1701.

I. Trapani, A. Puppo and A. Auricchio, Vector platforms for gene therapy of inherited retinopathies, 2014, 43, 108-128.

M. F. Dias, et al., Molecular genetics and emerging therapies for retinitis pigmentosa: Basic research and clinical perspectives, 2018, 63, 107-131.

M. J. Seiler, et al., Photoreceptor function of retinal transplants implicated by light-dark shift of S-antigen and rod transducin, Vision Res, 1999, 39, 2589-2596.

G. Woch, et al., Retinal Transplants Restore Visually Evoked Responses in Rats with Photoreceptor Degeneration, Invest Ophthalmol Vis Sci, 2001, 42, 1669-1676.

B. T. Sagdullaev, et al., Retinal Transplantation-Induced Recovery of Retinotectal Visual Function in a Rodent Model of Retinitis Pigmentosa, Invest Ophthalmol Vis Sci, 2003, 44, 1686-1695.

B. B. Thomas, et al/. Superior colliculus responses to light—preserved by transplantation in a slow degeneration rat model, Exp Eye Res, 2004, 79, 29-39.

P. B. Yang, et al., Tropic factors GDNF and BDNF improve function of retinal sheet transplants, Exp Eye Res, 2010, 91, 727-738.

M. J. Seiler, et al., Vision Recovery and Connectivity by Fetal Retinal Sheet Transplantation in an Immunodeficient Retinal Degenerate Rat Model, Invest Ophthalmol Vis Sci, 2017, 58, 614-630.

B. B. Thomas, et al., Retinal Transplantation: A treatment strategy for retinal degenerative diseases, Retinal Degenerative Diseases, eds. J. G. Hollyfield, R. E. Anderson and M. M. LaVail, Springer, New York, NY, 2006, pp. 367-376.

R. B. Aramant , et al., Progress in retinal sheet transplantation, Prog Retin Eye Res, 2004, 23, 475-494.

M. J. Seiler, et al., A new immunodeficient pigmented retinal degenerate rat strain to study transplantation of human cells without immunosuppression, Optics and Photonics News, 2008, 19, 37-47.

M. J. Seiler, et al., Cell replacement and visual restoration by retinal sheet transplants, Prog Retin Eye Res, 2012, 31, 661-687.

N. D. Radtke, et al., Vision Improvement in Retinal Degeneration Patients by Implantation of Retina Together with Retinal Pigment Epithelium, Am J Ophthalmol, 2008, 146, 172-182.

B. A. Tucker, et al., Transplantation of Adult Mouse iPS Cell-Derived Photoreceptor Precursors Restores Retinal Structure and Function in Degenerative Mice, PLoS One, 2011, 6, e18992.

R. A. Pearson, et al., Restoration of vision after transplantation of photoreceptors, Nature, 2012, 485, 99-103.

M. S. Singh, et al., Reversal of end-stage retinal degeneration and restoration of visual function by photoreceptor transplantation, Proc Natl Acad Sci U S A, 2013, 110, 1101-1106.

D. A. Lamba, et al., Transplantation of Human Embryonic Stem Cell-Derived Photoreceptors Restores Some Visual Function in Crx-Deficient Mice, Cell Stem Cell, 2009, 4, 73-79.

R. E. MacLaren, et al., Retinal repair by transplantation of photoreceptor precursors, Nature, 2006, 444, 203-207.

F. C. Mansergh, et al., Loss of photoreceptor potential from retinal progenitor cell cultures, despite improvements in survival, Exp Eye Res, 2010, 91, 500-512.

(56) References Cited

OTHER PUBLICATIONS

J. A. Thomson, et al., Embryonic Stem Cell Lines Derived from Human Blastocysts, Science, 1998, 282, 1145-1147.

K. Takahashi, et al., Induction of Pluripotent Stem Cells from Adult Human Fibroblasts by Defined Factors, Cell, 2007, 131, 861-872.

C. M. Fligor, et al., Three-Dimensional Retinal Organoids Facilitate the Investigation of Retinal Ganglion Cell Development, Organization and Neurite Outgrowth from Human Pluripotent Stem Cells, Scientific reports, 2018, 8, 14520.

K. Wahlin, et al., Photoreceptor Outer Segment-like Structures in Long-Term 3D Retins from Human Pluripotent Stem Cells, Journal, 2017.

T. Nakano, et al., Self-Formation of Optic Cups and Storable Stratified Neural Retina from Human ESCs, Cell Stem Cell, 2012, 10, 771-785.

B. T. McLelland, et al., Transplanted hESC-Derived Retina Organoid Sheets Differentiate, Integrate, and Improve Visual Function in Retinal Degenerate Rats, Investigative ophthalmology & visual science, 2018, 59, 2586-2603.

J. Assawachananont, et al., Transplantation of Embryonic and Induced Pluripotent Stem Cell-Derived 3D Retinal Sheets into Retinal Degenerative Mice, Stem cell reports, 2014, 2, 662-674.

H. Shirai, et al., Transplantation of human embryonic stem cell-derived retinal tissue in two primate models of retinal degeneration, Proceedings of the National Academy of Sciences, 2016, 113, E81-E90.

S. Llonch, et al., Organoid technology for retinal repair, Dev Biol, 2018, 433, 132-143.

C. B. Mellough, et al., Systematic Comparison of Retinal Organoid Differentiation from Human Pluripotent Stem Cells Reveals Stage Specific, Cell Line and Methodological Differences, Stem cells translational medicine, 2019, 8, 694-706.

Z. Ao, et al., One-Stop Microfluidic Assembly of Human Brain Organoids To Model Prenatal Cannabis Exposure, Anal Chem, 2020, 92, 4630-4638.

M. E. Boutin, et al., 3D Engineering of Ocular Tissues for Disease Modeling and Drug Testing, Adv Exp Med Biol, 2019, 1186, 171-193.

T. DiStefano, et al., Accelerated and Improved Differentiation of Retinal Organoids from Pluripotent Stem Cells in Rotating-Wall Vessel Bioreactors, Stem cell reports, 2018, 10, 300-313.

L. Goto-Silva, et al., Computational fluid dynamic analysis of physical forces playing a role in brain organoid cultures in two different multiplex platforms, BMC Dev Biol, 2019, 19, 3.

M. A. Phelan, et al., Mini and customized low-cost bioreactors for optimized high-throughput generation of tissue organoids, Stem Cell Investig, 2018, 5, 33.

A. Artero Castro, et al., Deciphering Retinal Diseases Through the Generation of Three-Dimensional Stem Cell-Derived Organoids: Concise Review, Stem Cells, 2019, 37, 1496-1504.

E. Berger, et al., Millifluidic culture improves human midbrain organoid vitality and differentiation, Lab on a Chip, 2018, 18, 3172-3183.

B. Sidar, et al., Long-term flow through human intestinal organoids with the gut organoid flow chip (GOFlowChip), Lab Chip, 2019, 19, 3552-3562.

M. J. Beauchamp, et al., Moving from millifluidic to truly microfluidic sub-100-μm cross-section 3D printed devices, Ana Bioanal Chem, 2017, 409, 4311-4319.

D. Qin, et al., Soft lithography for micro- and nanoscale patterning, Nature protocols, 2010, 5, 491-502.

J. Collin, et al., Using Zinc Finger Nuclease Technology to Generate CRX-Reporter Human Embryonic Stem Cells as a Tool to Identify and Study the Emergence of Potoreceptors Precursors during Pluripotent Stem Cell Differentiation, Stem Cells, 2016, 34, 311-321.

J. Collin, et al., Deconstructing Retinal Organoids: Single Cell RNA-Seq Reveals the Cellular Components of Human Pluripotent Stem Cell-Derived Retina, Stem Cells, 2019, 37, 593-598.

J. Collin, et al., CRX Expression in Pluripotent Stem Cell-Derived Photoreceptors Marks a Transplantable Subpopulation of Early Cones, Stem Cells, 2019, 37, 609-622.

X. Zhong, et al., Generation of three-dimensional retinal tissue with functional photoreceptors from human iPSCs, Nature communications, 2014, 5, 4047.

M. A. Digman, et al., The Phasor Approach to Fluorescence Lifetime Imaging Analysis, Biophys J, 2008, 94, L14-16.

C. Stringari, et al., Phasor Fluorescence Lifetime Microscopy of Free and Protein-Bound NADH Reveals Neural Stem Cell Differentiation Potential, PloS one, 2012, 7, e48014.

R. Datta, et al., Fluorescence lifetime imaging of endogenous biomarker of oxidative stress, Sci Rep, 2015, 5, 9848.

* cited by examiner

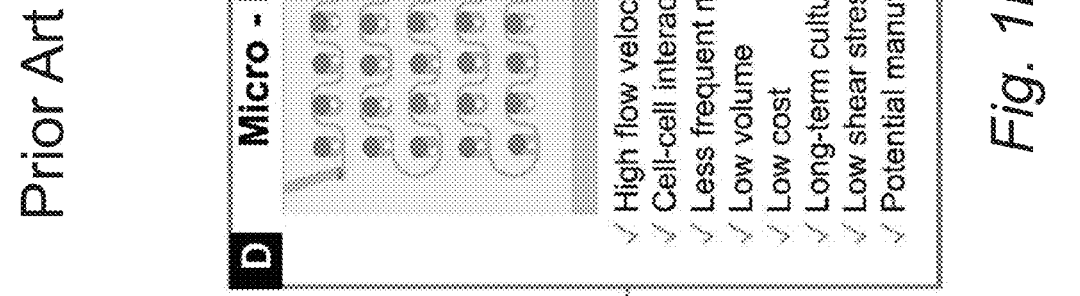
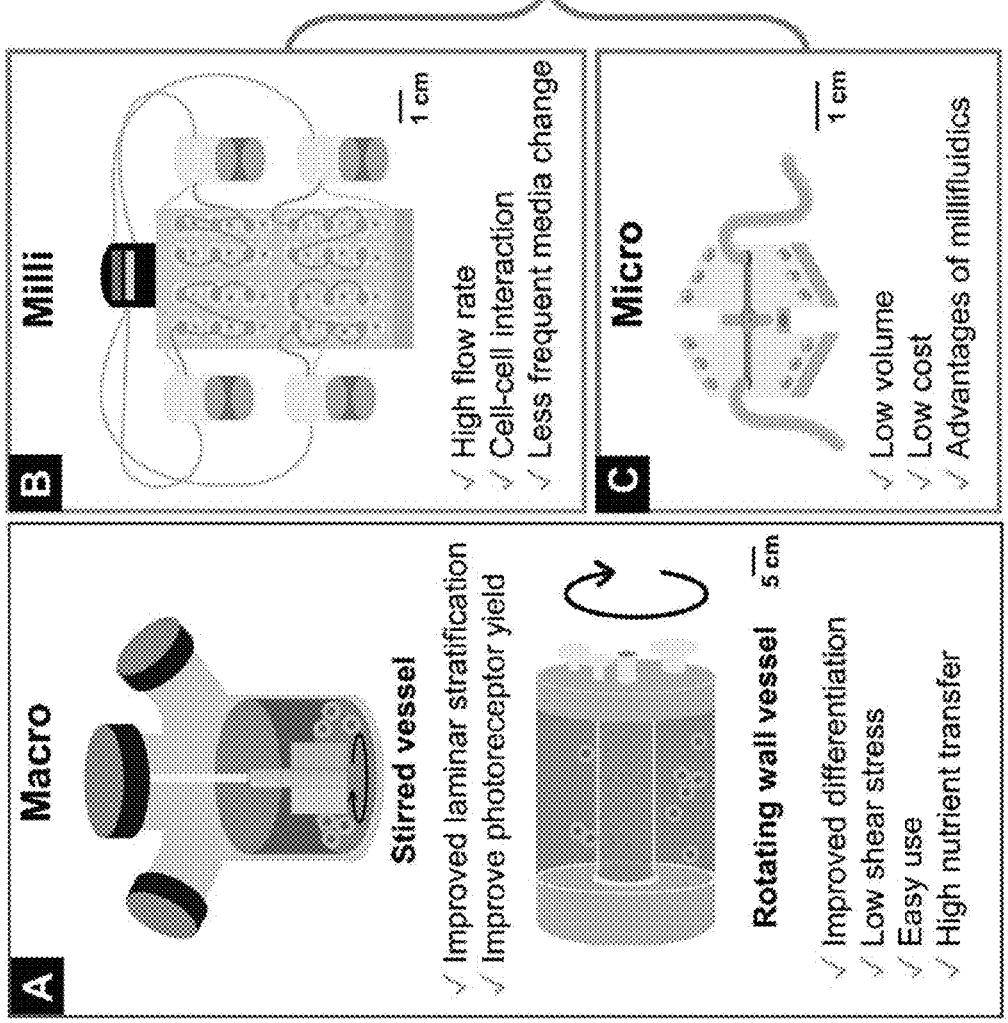
Fig. 1A  Fig. 1B  Fig. 1C  Fig. 1D

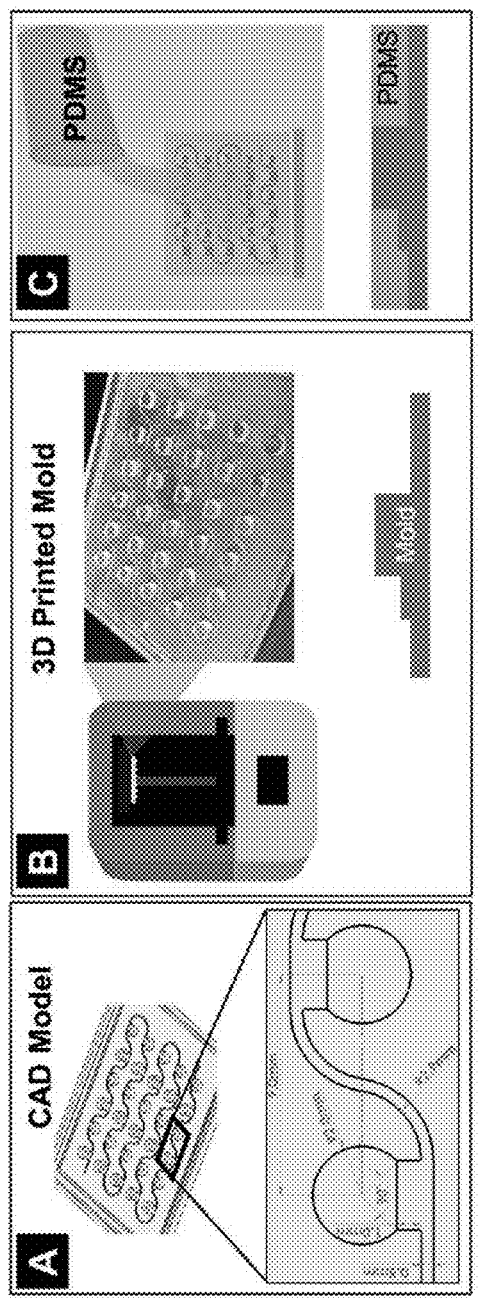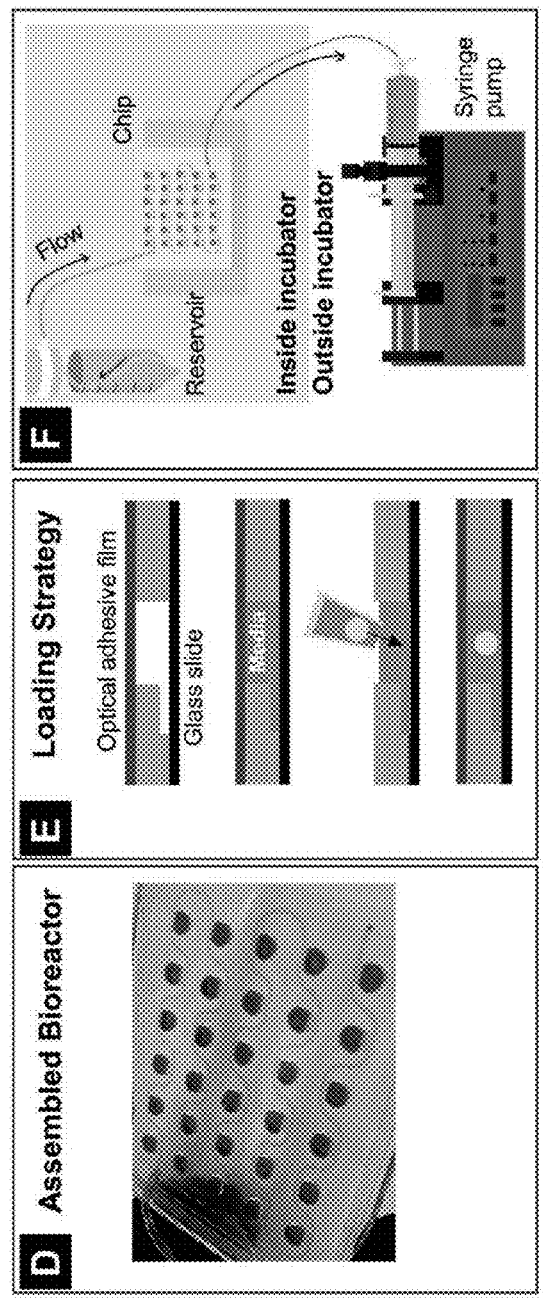

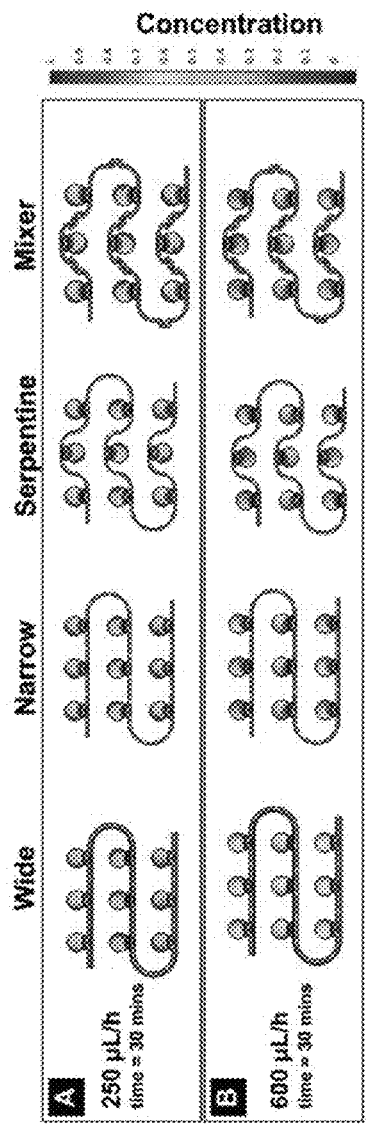 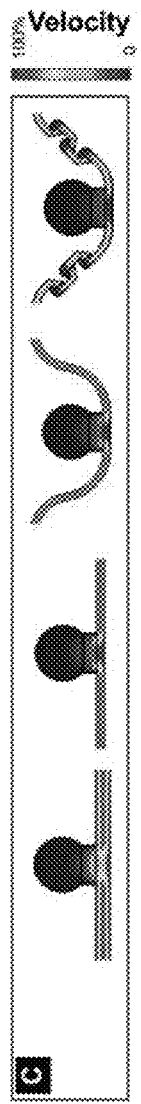 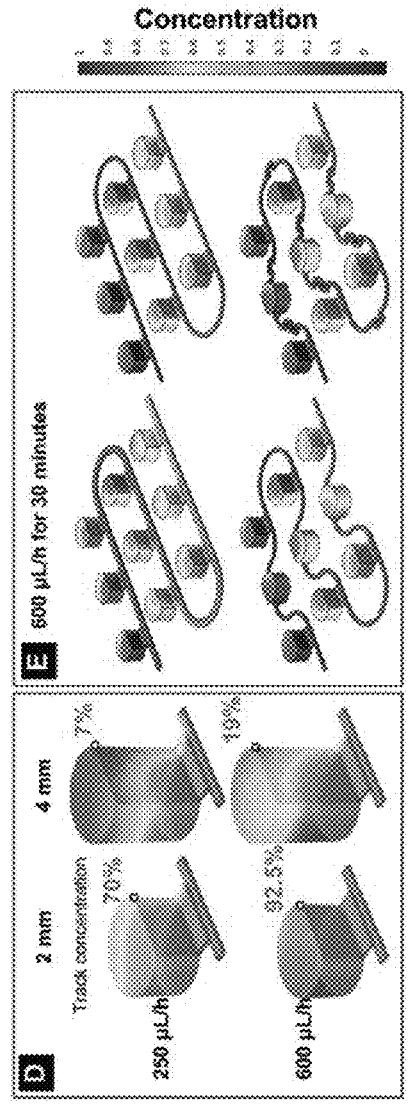
Fig. 4A Fig. 4B Fig. 4C Fig. 4D Fig. 4E

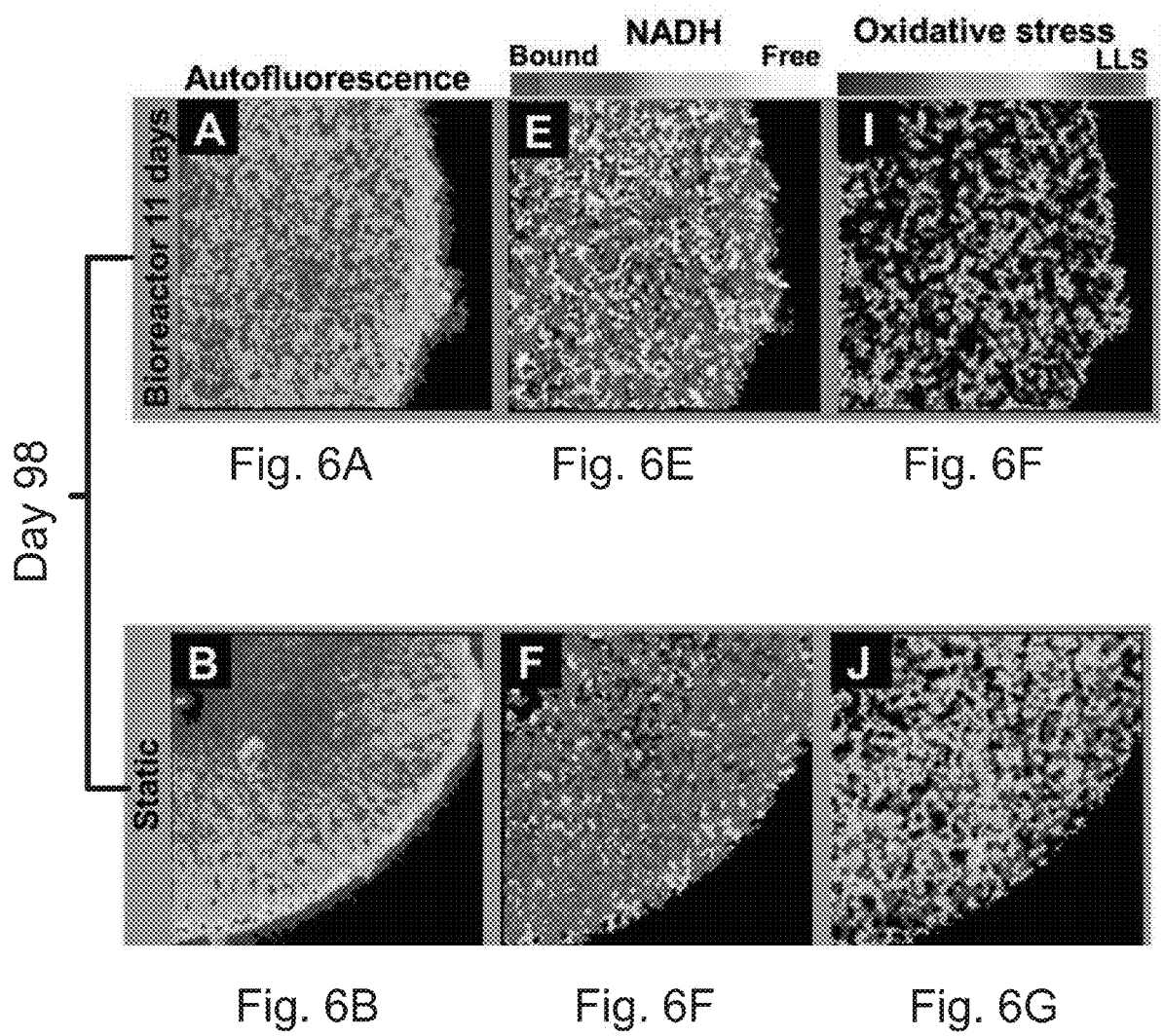

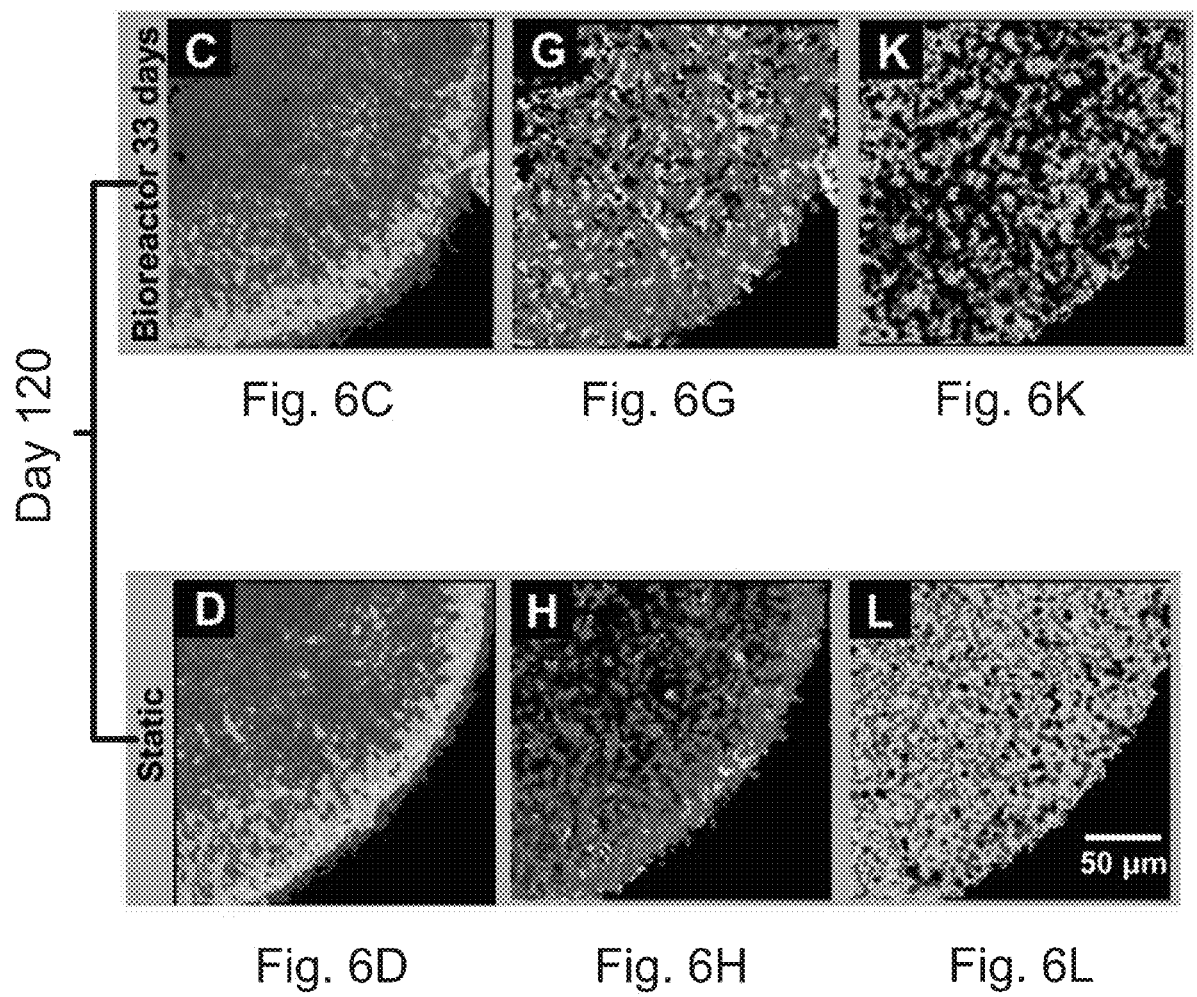

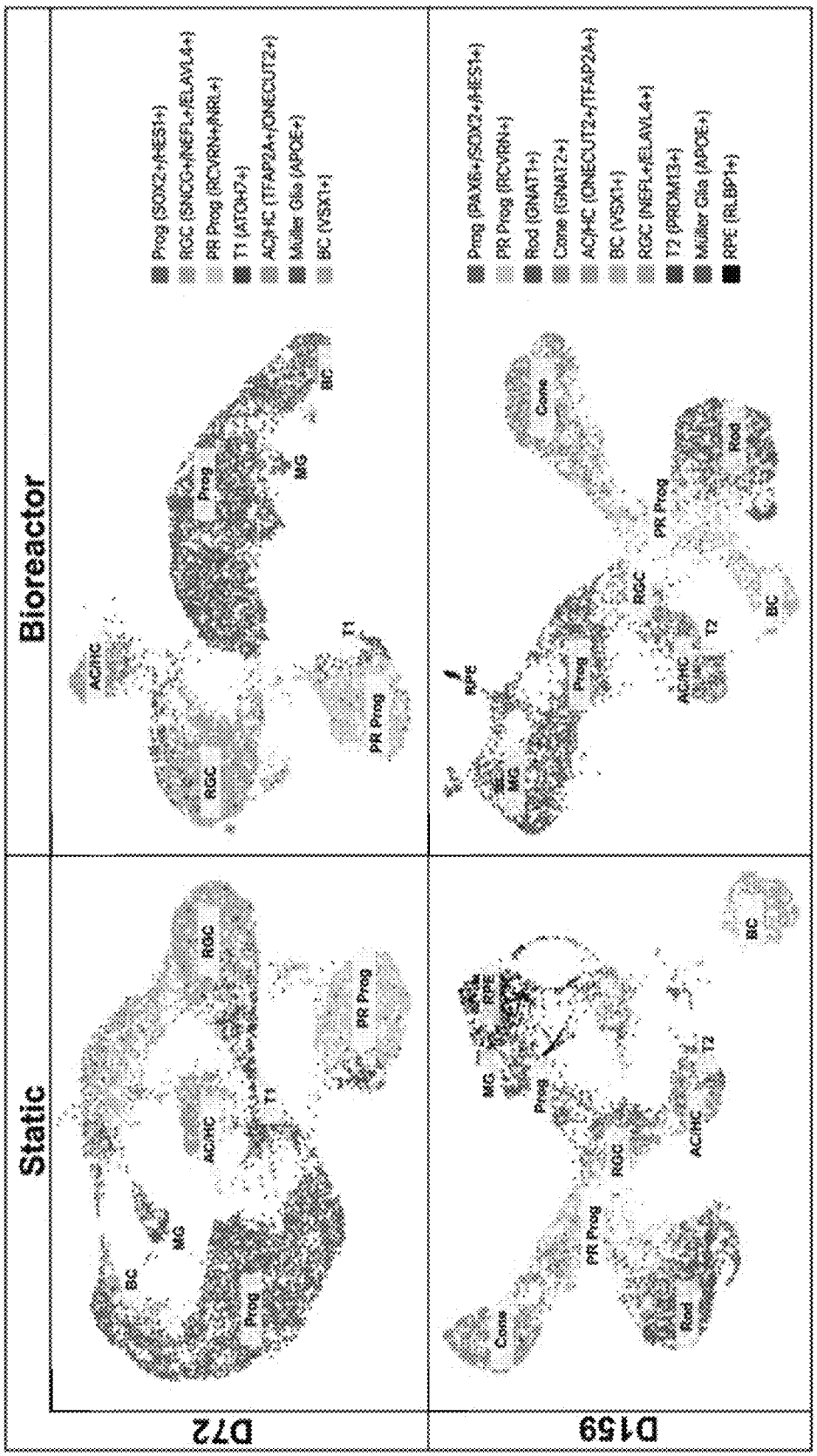

Fig. 8A  Fig. 8B
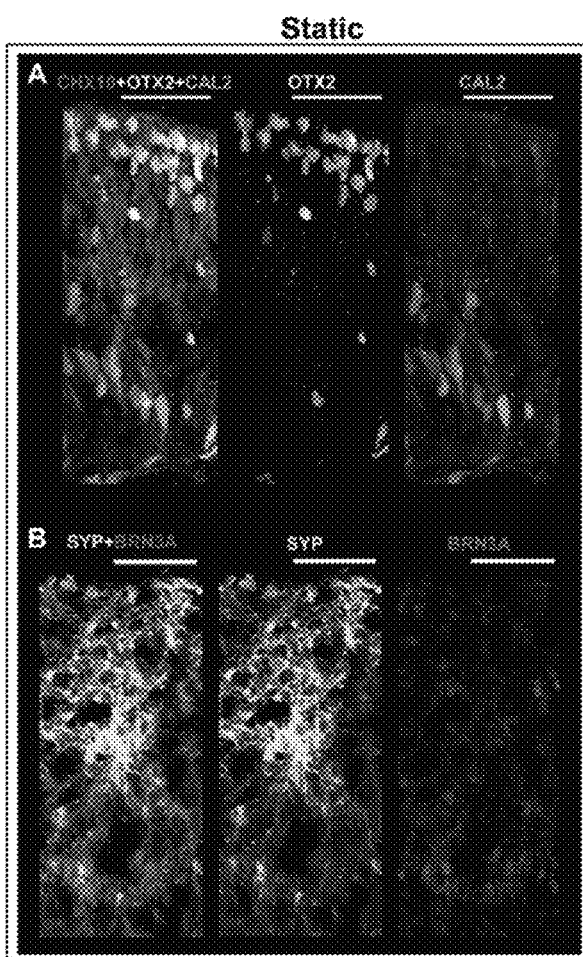
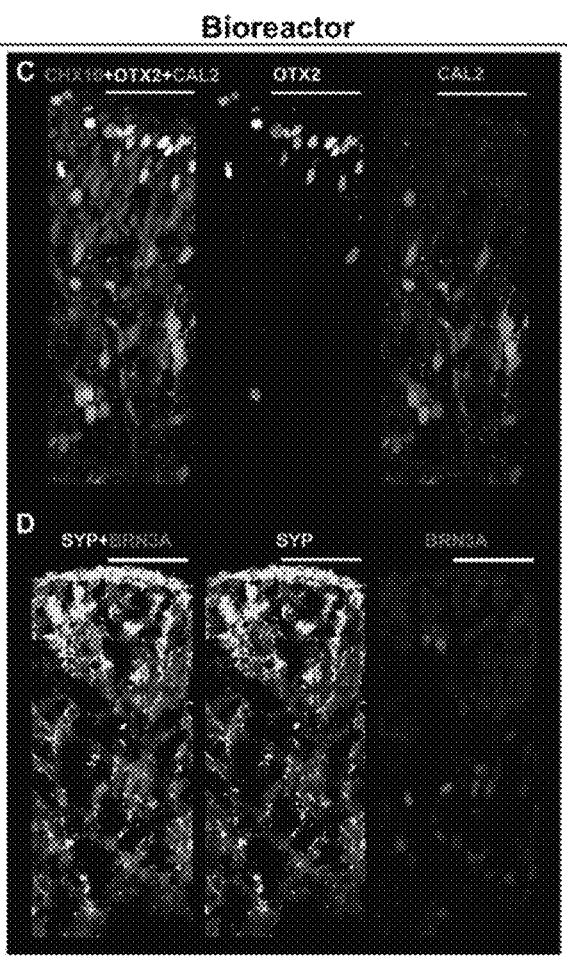
Fig. 8B  Fig. 8D

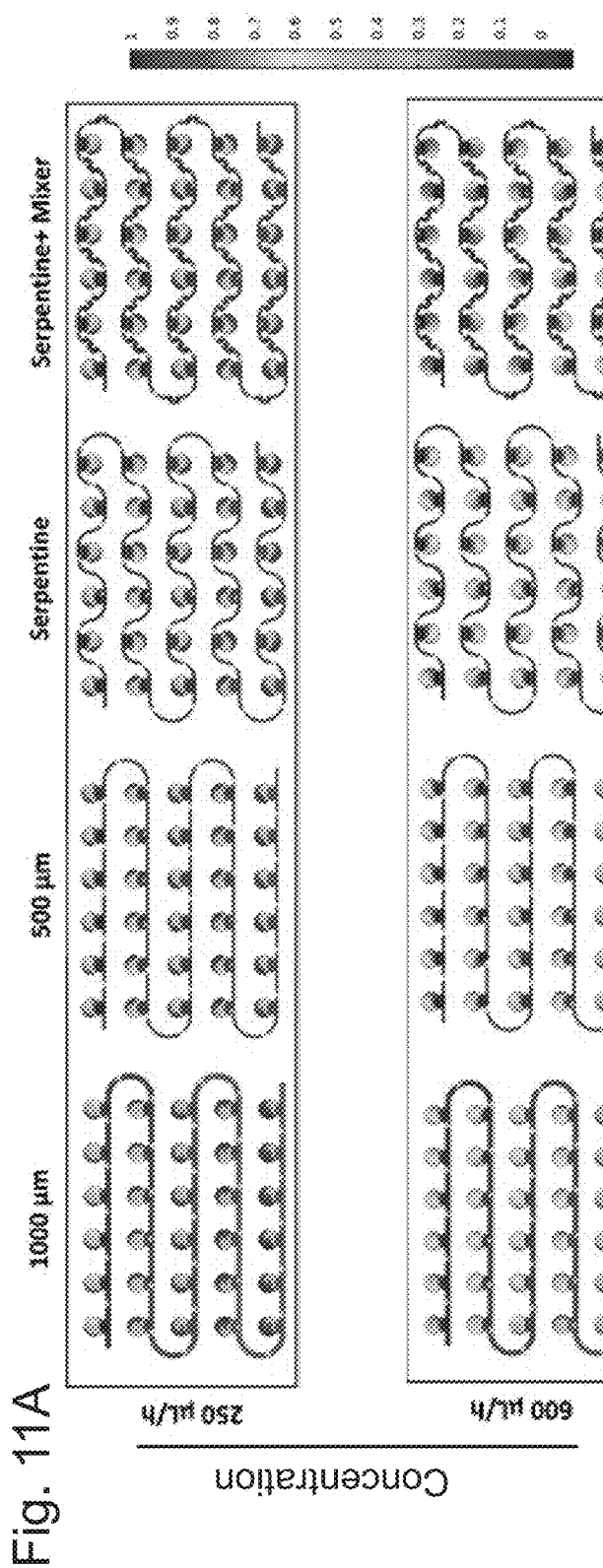
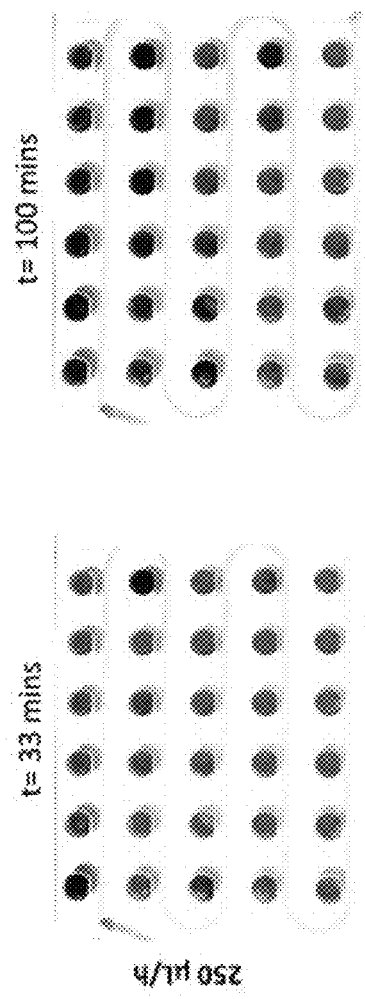
Fig. 11A, Fig. 11B, Fig. 11C-1, Fig. 11C-2

Fig. 12E
Fig. 12G
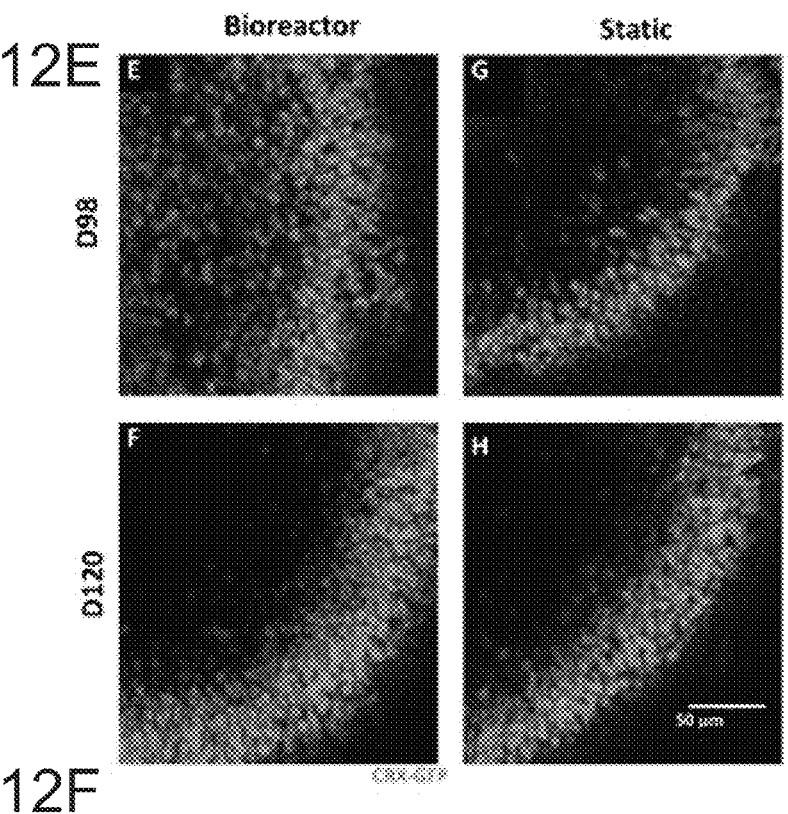
Fig. 12F
Fig. 12H
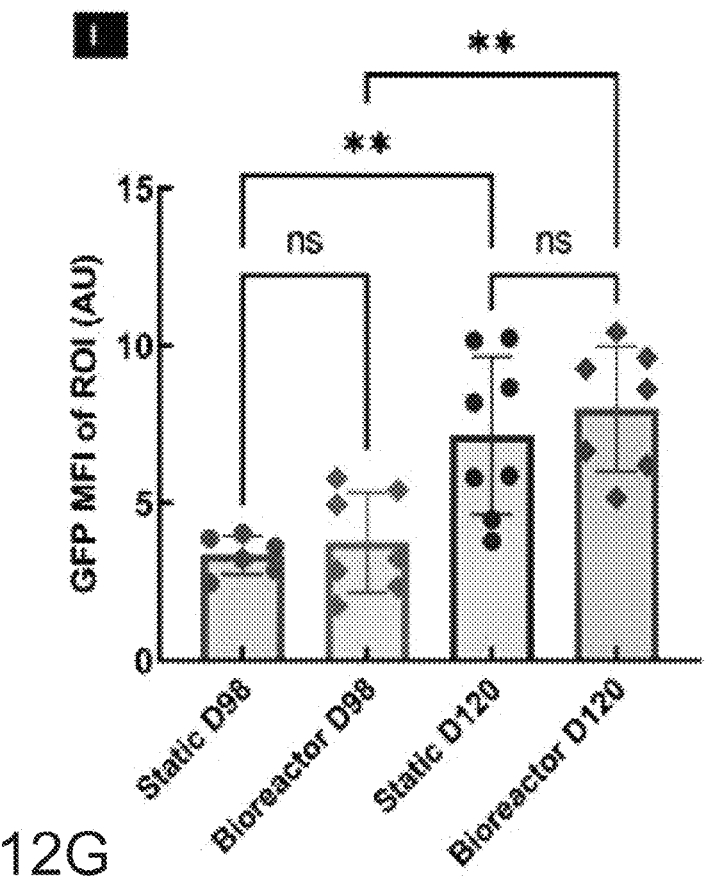
Fig. 12G

Table 1. Summary of Experimental Groups

| Cell Line | Total Time | Static & Bioreactor | PC | FLIM | IH | GFP | scRNA | qPCR | SEM TEM |
|---|---|---|---|---|---|---|---|---|---|
| CRX-GFP | D38-D72 | D41-D72 (31 days) | D41 | D38 D71 | D72 D71 | | D72 | | |
| | D87-D124 | D87-D124 (37 days) | D88 D124 | D98 D120 | | D98 D120 | | D124 | |
| | D125-D159 | D128-D159 (31 days) | D158 | D125 D158 | D159 | | D159 | | D159 |
| CSC-14 | D70-D105 | D70-D105 (35 days) | | | | | | D105 | |

*PC – phase contrast imaging; FLIM – fluorescence lifetime imaging; IH – immunohistology; scRNA – single-cell RNA sequencing.

*Fig. 15*

Table 2: Information of qPCR primers

| Gene name | Official full name | GeneGlobe ID |
|---|---|---|
| CHX10 (VSX2) | Visual system homeobox 2 | QT00221081 |
| NRL | Neural retina leucine zipper | QT01005165 |
| RAX | Retina and anterior neural fold homeobox | QT00212667 |
| RCVRN | Recoverin | QT00014098 |
| ARR3 | Arrestin 3 | QT00000182 |
| SAG | S-antigen visual arrestin | QT01007958 |
| PRPH2 | Peripherin 2 | QT00094094 |
| GNAT | G-protein subunit alpha transducin | QT00235606 |
| GNAT2 | G-protein subunit alpha transducin 2 | QT00008764 |
| RHO | Rhodopsin | QT01017058 |
| OPN1SW | Opsin 1, short wave sensitive | QT00017304 |
| OPN1MW | Opsin 1, medium wave sensitive | QT00040887 |
| OPN1LW | Opsin 1, long wave sensitive | QT01007356 |
| RPL7 | Ribosomal protein L7 | QT01670137 |

Fig. 16

Table 3: Information of Antibodies

| Antibody | Species | Concentration | Manufacturer | Catalogue # | RRID |
|---|---|---|---|---|---|
| Rhodopsin (Rho4D2) | Mouse | 1:100 | Gift of Dr. Molday [1], University of British Columbia | N/A | AB_2315273 AB_2315274 |
| Human NRL | Goat | 1:100 | R&D Systems | AF2945 | AB_2155098 |
| Recoverin | Rabbit | 1:2000 | Millipore | AB5585 | AB_2253622 |
| Calretinin | Goat | 1:100 | Novus | AF5065 | AB_2068516 |
| OTX2 | Rabbit | 1:1000 | ThermoFisher | 701948 | AB_2608961 |
| CHX10 | Mouse | 1:100 | Santa Cruz | sc-365519 | AB_10842442 |
| RG-opsin | Rabbit | 1:1000 | Millipore | AB5405 | AB_177456 |
| Synaptophysin | Goat | 1:100 | Novus | AF5555 | AB_2198864 |
| PKC alpha | Rabbit | 1:200 | Oxford Biomedical | PK13 | N/A |
| CRALBP | Rabbit | 1:2000 | Fitzgerald | 70R-19906 | N/A |

Fig. 17

Table 4: Key Reagents and Resources

| Reagents or Resource | Source | Identifier |
|---|---|---|
| mTeSR 1 media | STEMCELL Technologies | Cat# 85850 |
| ReLeSR | STEMCELL Technologies | Cat# 100-0484 |
| Vitronectin XF™ | STEMCELL Technologies | Cat# 07180 |
| Accutase | Nacalai USA, Inc. | Cat# NU1267954 |
| Growth factor reduced Matrigel | Corning | Cat# 354230 |
| Dulbecco's modified eagle Medium (DMEM) | Gibco | Cat# 12100-038 |
| F12 Nutrient Mixture | Gibco | Cat# 21700-026 |
| N2 supplement | Gibco | Cat# 17-502-048 |
| Minimum essential media non – essential amino acids (NEAA) | Gibco | Cat# 11140-050 |
| L-glutamine 200mM (100X) | Gibco | Cat# 25030-081 |
| Heparin | Sigma-Aldrich | CAS 9041-08-1 |
| B27 supplement (50X) (minus Vitamin A) | Gibco | Cat# 1587-010 |
| B27 Plus supplement (50X) | Gibco | Cat# A3582801 |
| Taurine | Sigma-Aldrich | CAS# 107-35-7 |
| Heat inactivated 10% fetal bovine serum (FBS) | Gibco | Cat# 10438-026 |
| bFGF | Peprotech | Cat# 100-18B |
| Activin-A | Peprotech | Cat# 120-14E |
| Collagenase IV | Gibco | Cat# 17104019 |
| Anti-cell adherence solution | STEMCELL Technologies | Cat# 07010 |
| Dulbecco's phosphate-buffered saline (DPBS) without calcium and magnesium (10X) | STEMCELL Technologies | Cat# 37354 |
| TRIzol reagent | Fisher | Cat# 15596026 |
| DNase I | Invitrogen TURBO | Cat# AM2238 |
| Phenol/Chloroform/Isoamyl Alcohol | Fisher | Cat# BP17521-400 |
| RT$^2$ cDNA synthesis kit | Qiagen | Cat# 330401 |
| ROX qPCR master mix | Qiagen | Cat# 330530 |
| Worthington papain disassociation System | Worthington | http://www.worthington-biochem.com/PDS/cat.html |

Fig. 18A

| | | |
|---|---|---|
| 10X Genomics Chromium Single Cell 3' Reagent Kit v3.1 | 10X Genomics | N/A |
| Kapa qPCR Library | Roche | Cat# 07960140001 |
| Histo-VT One | Nacalai | Product# 06380-05 |
| Vectashield Vibrance Antifade Mounting Medium | Vector Labs | Cat# H-1700 |
| Standard clear resin | Formlabs | Cat# RS-F2-GPCL-04 |
| Optimum cutting temperature (OCT) compound (PolarStat Plus, StatLab, McKinney, TX, USA) | Ted Pella Inc. | Product# 27301-1 |
| *Critical Commercial Assays* | | |
| 0.6X SPRIselect | Beckman Coulter | Cat# B23318 |
| Qubit DNA HS assay | Life Technologies | Cat# Q32851 |
| Agilent 2100 Bioanalyzer DNA HS | Agilent | Cat# 5067-1504 |
| *Experimental Models: Cell Lines* | | |
| hESC, CRX-GFP H9 | Dr. Majlinda Lako Newcastle University [2-4], UK | Derived from NIH Registration #004 |
| hESCs, CSC-14 | AVITA Biomedical Inc. | NIH registration #0284 |
| *Equipment and Culture Plates* | | |
| Formlabs Form 3B | Formlabs | N/A |
| Harrick | Harrick Plasma | N/A |
| #1.5, 64*50 mm, ClariTex | Ted Pella Inc. | Cat# 260378 |
| Humidified 5% $CO_2$ incubator | Nuaire | N/A |
| EZSPHERE 12-well plate (D: 800µm, d: 400µm) | Nacalai USA, Inc. | Cat# TCI-4815-903SP-10P |
| Ultra-low attachment Corning Costar 24-well plate | Corning | Cat# 07-200-602 |
| CoolCLAVE Plus | Genlantis | N/A |
| 50 mL Steriflip-GP sterile centrifuge tube with filter cap pore size 0.22 µm | Millipore Sigma | Cat# SCGP00525 |
| MicroAmp™ optical adhesive film | Thermo Fisher Scientific | Cat# 4311971 |
| ESCO Class II Type A2 biosafety Cabinet | ESCO Micro Pte. Ltd. | N/A |

Fig. 18B

| photomultiplier tube | Hamamatsu Photonics | H7422p-40 |
|---|---|---|
| FastFLIM FLIMbox | ISS | N/A |
| Nunc® Lab-Tek® II Chambered Coverglass | Thermo Fisher | Cat# 155411 |
| Olympus IX71 | Olympus | N/A |
| QICAM FAST1394 CCD camera | Teledyne QImaging | N/A |
| Bio-Rad C1000 Thermocycler | Bio-Rad Laboratories | N/A |
| Dynabeads MyOne SILANE | Life Technologies | N/A |
| Illumina NovaSeq 6000 | Illumina | N/A |
| Zeiss LSM700 | Carl Zeiss | N/A |
| JEOL 2100 | JEOL USA, Inc. | N/A |
| FEI Magellan 400 XHR | FEI Company | N/A |
| *Software and Algorithms* | | |
| COMSOL Multiphysics 5.6 | COMSOL, Inc. | N/A |
| SolidWorks 2020 | SolidWorks Corp. | N/A |
| Graphpad Prism | Graphpad Software LLC | N/A |
| FASTQC | Babraham Bioinformatics | https://github.com/s-andrews/FastQC 1 |
| cellRanger v.3.1.0. | 10X Genomics | N/A |
| Zen 3.3 Software | Zeiss | N/A |
| Adobe Photoshop | Adobe | N/A |
| Etomo | University of Colorado, Boulder | N/A |

Fig. 18C

3D PRINTED MICRO-MILLIFLUIDIC BIOREACTORS FOR LONG-TERM RETINAL ORGANOID MAINTENANCE

CROSS-REFERENCE TO RELATED APPLICATIONS

This application claims the benefit of U.S. provisional application Ser. No. 63/241,142 filed Sep. 7, 2021, the disclosure of which is hereby incorporated in its entirety by reference herein.

STATEMENT REGARDING FEDERALLY SPONSORED RESEARCH OR DEVELOPMENT

This invention was made with Government support under Grant No. KL2 TR001416 awarded by the National Institutes of Health (NIH). The Government has certain rights in this invention.

TECHNICAL FIELD

In at least one aspect, the present invention relates to micro-milli-fluidic bioreactors.

BACKGROUND

Retinal degeneration (RD) is a leading cause of vision impairment and blindness worldwide. Visual degeneration can originate in any of the cell types in the retina. Some of the more common visual degenerations arise from death and/or dysfunction of the photoreceptors (PR) and retinal pigmented epithelial (RPE) cells. Irreversible cell damage is the root to vision loss in diseases like age-related macular degeneration (AMD) and retinitis pigmentosa (RP)[1,2].

Retinal sheets and dissociated retinal cells are candidates for retinal tissue replacement therapy. However, both tissue sources have inherent limitations. Historically, retinal sheets derived from fetal neurosensory retina and RPE transplanted into the subretinal space demonstrated utility to restore vision and neurosensory functions[3-9] in animals[10-12] and humans[13]. However, the use of fetal tissue carried complex social, ethical, and political implications. Transplantation of dissociated photoreceptor precursors overcame the ethical issues and demonstrated some visual function improvements[14,15], but dissociated cell transplantation[16-19] suffered from insufficient cell type differentiation, lack of cellular polarization, and eventual cell death.

With the advent of new techniques to manipulate human embryonic (hESCs)[20] and induced pluripotent stem cells (iPSCs),[21] stem cell-derived retinal organoids (RtOgs) have emerged as tools that exhibit the combined advantages of retinal sheets and differentiated retinal cells. RtOgs are 3D spheroid tissues that arise from stem cells and self-organize into layered retinal tissues containing retinal ganglion cells, rods, and cones[22-24]. Transplantation of RtOgs has been shown to restore vision in retina degenerated rats[25], mouse,[26] and primate[27] models with RD. Even so, current state-of-the-art RtOg production methods are highly heterogeneous due to their use of different cell lines, tissue maintenance methods, high manual labor, and imprecise tissue selection for use in multiple applications[28]. A comparative study revealed that RtOgs differentiated from iPSCs showed stage-specific, cell line, and methodological differences[29]. This heterogeneity and imprecision limit human RtOg procurement for preclinical trials[28] and in vitro investigations. Many approaches, including bioreactors[30-36] and optimized production protocols[28,37] are investigated to standardize RtOg production and maintenance over months. Controlled and predictable RtOg production is important to ensure a quality-controlled tissue product that is suitable for transplantation.

In recent years, many in vitro cell culture platforms have emerged for organoid differentiation and maintenance at the macro-[38], milli-[39], and microscales[40]. Macro-scaled platforms are typically utilized for their ease and effectiveness in producing organoids, while milli-scaled systems (? 1 mm) are employed for relatively high flow rates, cell-cell interaction, and less frequent media changes and thus less organoid perturbation and lower probability for damage[31]. Considering the costs associated with the relatively high media volumes required by the macro-scaled bioreactors, microscale devices (<100 μm) are steadily growing in popularity[41]. Microfluidic devices share the advantages of millifluidic devices, with the advantage of lower media consumption. However, the dimensional limits of traditionally fabricated microfluidics devices hinder their application to organoids research since organoids are 3D spherical tissues that can grow up to several millimeters in size. FIG. 1 summarizes published organoid bioreactors and their advantages and disadvantages. The integration of micro- and millifluidic devices is a promising solution for organoid differentiation and maintenance.

Accordingly, there is a need for a bioreactor that permits long term organoid maintenance that ensures a quality-controlled tissue product that is suitable for research or transplantation.

SUMMARY

In at least one aspect, a bioreactor for use in long-term organoid culture and maintenance in a low shear stress environment that is compatible with multimodal imaging is provided. A higher flow rate through a narrower channel with culture chambers on alternating sides of the perfusion channel enables optimal and practical concentration uniformity between culture chambers. RtOgs on the provided shear stress-free micro-millifluidic bioreactor are successfully cultured for 1 month. Key similarities and differences between RtOgs maintained in traditional culture conditions or the bioreactor are identified. The micro-millifluidic bioreactor provided confers improvements in the culture and maintenance of RtOgs of useful quality.

In another aspect, a bioreactor device for culturing organoids, and in particular, retinal organoids is provided. The bioreactor device includes a solid substrate having a first face and a second face. The solid substrate at least partially defines a perfusion channel, a plurality of chambers, a fluidic inlet, and a fluidic outlet. A first sheet is disposed over the first face and a second sheet is disposed over the second face. Characteristically, the combination of the solid substrate, the first sheet, and the second sheet defines the perfusion channel and each chamber of the plurality of chambers. The plurality of chambers are arranged in rows of chambers in which adjacent chambers are positioned at opposite sides of the perfusion channel. The perfusion channel extends from the fluidic inlet and the fluidic outlet having a serpentine path along each row of chambers, with each chamber being in fluid communication with the perfusion channel.

In another aspect, a fabrication method based on stereolithography (SLA) 3D printing allowed for the creation of a mold incorporating micro-, milli- and macroscopic features. This method also enabled the rapid prototyping of bioreactor designs for iterative optimization. This additive manufacturing offers improvements over traditional microfabrication methods[69].

In another aspect, improvements over earlier work that explored the optimization of in vitro cell culture platforms for organoid differentiation and maintenance at the macro-[38], milli-[39], and microscalee are provided. The dimensional limits of traditionally fabricated microfluidics devices hinder their application to organoids research since organoids are 3D spherical tissues that can grow up to several millimeters in size. Therefore, integrated micro- and millifluidics are integrated to design and fabricate a shear stress-free micro-millifluidic bioreactor for use in RtOg culture and maintenance. A high resolution (25 μm) stereolithography (SLA) 3D printer is used to fabricate the mold for Polydimethylsiloxane (PDMS) molding, which combined micro and millimeter features in one design. The fluidic design parameters were simulated in COMSOL to optimize the fluidic transports in the chip design. Three different factors that could affect mass transfer efficiency and uniformity were evaluated. RtOgs in 3 different differentiation stages on the designed chip platform for more than one month (31~37 days) were then successfully cultured, showing that the shear stress-free micro-millifluidic bioreactor improves RtOg culture and maintenance.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be made to the following detailed description, read in conjunction with the following drawings, wherein like reference numerals denote like elements and wherein:

FIGS. 1A, 1B, 1C, and 1D. Review of Organoid Bioreactors. (A) Macroscale bioreactors: stirred/spinning and rotating wall vessels 38; (B) Millifluidic bioreactor 39; (C) Microfluidic bioreactor 40; (D) Micro-millifluidic bioreactor in described herein.

FIGS. 3A, 3B, 3C, 3D, 3E, and 3F. Fabrication methods. (A) Mold design with CAD software; (B) Mold printing; (C) PDMS casting on the mold; (D) Assembled bioreactor; (E) Cross-section view of organoid loading procedure whereby microchannels were filled with media first, then an organoid was placed in the open well, and the wells were sealed using adhesive optical film; (F) On-chip culturing system assembly.

FIGS. 4A, 4B, 4C, 4D, 4E, 4F, and 4G. COMSOL simulation and dye test of 4 different channel designs. (A) Concentration distribution after 30 minutes of slow flow (250 μl/h); (B) Concentration distribution after 30 minutes of fast flow (600 μL/h); (C) Velocity distribution—zero velocity in all chambers demonstrated shear stress-free culture environment. A single culture chamber and adjacent flow channels is shown because focal flow velocity was identical for every culture chamber and interconnecting microfluidic channels in the linear series; (D) Mass transfer efficiency comparison between different height chambers under two different flow rates after 30 minutes. Black circles represent the location of concentration determination at 30 minutes; (E) 3D concentration pattern of four different designs. (F) Diffusion pattern of four different designs (flow rate was 600 μL/h); (G) Grayscale change of each well after 30 minutes and 48 minutes.

FIGS. 6A, 6B, 6C, 6D, 6E, 6F, 6G, 6H, 6I, 6J, 6K, 6L, 6M, 6N, and 6O. Qualitative and quantitative comparison of RtOgs in two culture methods. (A-D) Total NADH autofluorescence images demonstrated the cellular structures within RtOg cross sections; Pseudo color-coded free/bound NADH distribution (E-H) and LLS distribution (I-L) images were generated based on two photon lifetime within the 2-dimensional phasor space; (M) Scatter plots of and the clustering of different groups of RtOgs on the FLIM phasor diagram; (N) Plot of free/bound NADH ratio to evaluate metabolism (higher f/b value represented glycolysis, and lower f/b indicated greater oxidative phosphorylation.) Metabolism is not significantly different between static and bioreactor RtOgs after 1 month in culture for RtOgs of different ages; (O) Plot of LLS ratio to evaluate oxidative stress. LLS is significantly different between static and bioreactor maintained RtOgs of different ages after 1 month in culture. The values of f/b NADH ratio and LLS ratio reflect the average lifetimes of the organoids cross-section imaging frame. (One-way ANOVA test was performed: D38, n=8; Static D71, n=8; Bioreactor D71, n=13; Static D98, n=6; Bioreactor D98, n=8; Static D120 n=8; Bioreactor D120, n=7; D125, n=9; Static D158, n=10; Bioreactor D158, n=4; The RtOgs placed into the bioreactor D41-72 were imaged on D38 at the outset of the experiment. The RtOgs placed into the bioreactor D128-159 were imaged on D125 at the outset of the experiment.)

FIGS. 7A, 7B, 7C, 7D, 7E, 7F, and 7G. Gene profiles of RtOgs at different ages. Single-cell RNA seq generated UMAP identified cell types of RtOgs cultured under static on day 72 (A) and day 159 (B),under bioreactor culture on day 72 (C) and day 159 (D); (E) Cell number quantification: Cell number percentage of different type of cells, organized by the order of photoreceptor layers and the schematic image was shown on the right side; (F) qPCR gene analysis of CRX-GFP hESCs (negative control) generated RtOgs on day 124 of differentiation; (G) qPCR gene analysis of CSC-14 hESCs (negative control) generated RtOgs on day 105 of differentiation; Log 2 F.E— Log 2 (Fold Expression); Cell identities in (A-E): Prog—retinal progenitor cell; RGC—retinal ganglion cell; PR prog—photoreceptor progenitor cell; T1—transition phase 1; AC/HC—amacrine cells and horizontal cells; BC—bipolar cells; T2—transition phase 2; RPE—retinal pigment epithelium cell.

FIGS. 8A, 8B, 8C, and 8D. Immunohistology images of RtOgs on day 72 of differentiation after 1 month of tissue culture in static or bioreactor conditions. (A-B) Static cultured RtOgs; (C-D) Bioreactor cultured RtOgs. Antibody marked cells: CHX10—retinal progenitor cells; OTX2—photoreceptor progenitor cells; CAL2—amacrine cells; SYP—evidence of synaptogenesis; BRN3A—retinal ganglion cells. (scale bar: 50 μm)

FIGS. 11A, 11B, 11C-1, and 11C-2. COMSOL simulation and dye test of 5*6 arrays bioreactor. (A) Concentration distribution after 30 minutes of slow flow (250 μL/h); (B) Concentration distribution after 30 minutes of fast flow (600 μL/h); (C) Concentration pattern of the wide channel (1000 μm) design (5*6 array) after 33 minutes and 100 minutes of 250 μL/h flow.

FIGS. 12A, 12B, 12C, 12D, 12E, 12F, and 12G. Phase contrast and CRX-GFP fluorescence imaging results. (A) Human embryonic stem cell colony; (B) Day 0 of differentiation, dissociated CRX-GFP stem cells in EZSPHERE microwell plate (well size: 800 μm); (C) Day 8 of differentiation, embryonic bodies ready for seeding on Matrigel; (D) Day 38 differentiation on Matrigel; (E-H) Fluorescence images showed distinct cell nuclear layer corresponding to the CRX-GFP fusion protein localized in nuclei; (I) The mean fluorescence intensity of GFP signals at region of interest (One-way ANOVA test was performed: Static D98, n=6; Bioreactor D98, n=7; Static D120 n=8; Bioreactor D120, n=7). RtOgs in both static and bioreactor groups displayed a thick nuclear outer layer which expressed CRX gene on day 120 of differentiation (FIGS. 12F, H). The mean fluorescence intensity (MFI) of the selected outer surface region showed no significant difference between static and bioreactor cultured RtOgs on day 98 and 120. However, both groups had a significant increase of MFI over time, which suggests an increase of CRX expression during RtOgs differentiation (FIG. 12I).

FIG. 15. Table 1: Summary of Experimental Groups
FIG. 16. Table 2: Information of qPCR primers
FIG. 17. Table 3: Information of Antibodies
FIGS. 18A, 18B, and 18C. Table 4: Key Reagents and Resources

DETAILED DESCRIPTION

Figure 2A:
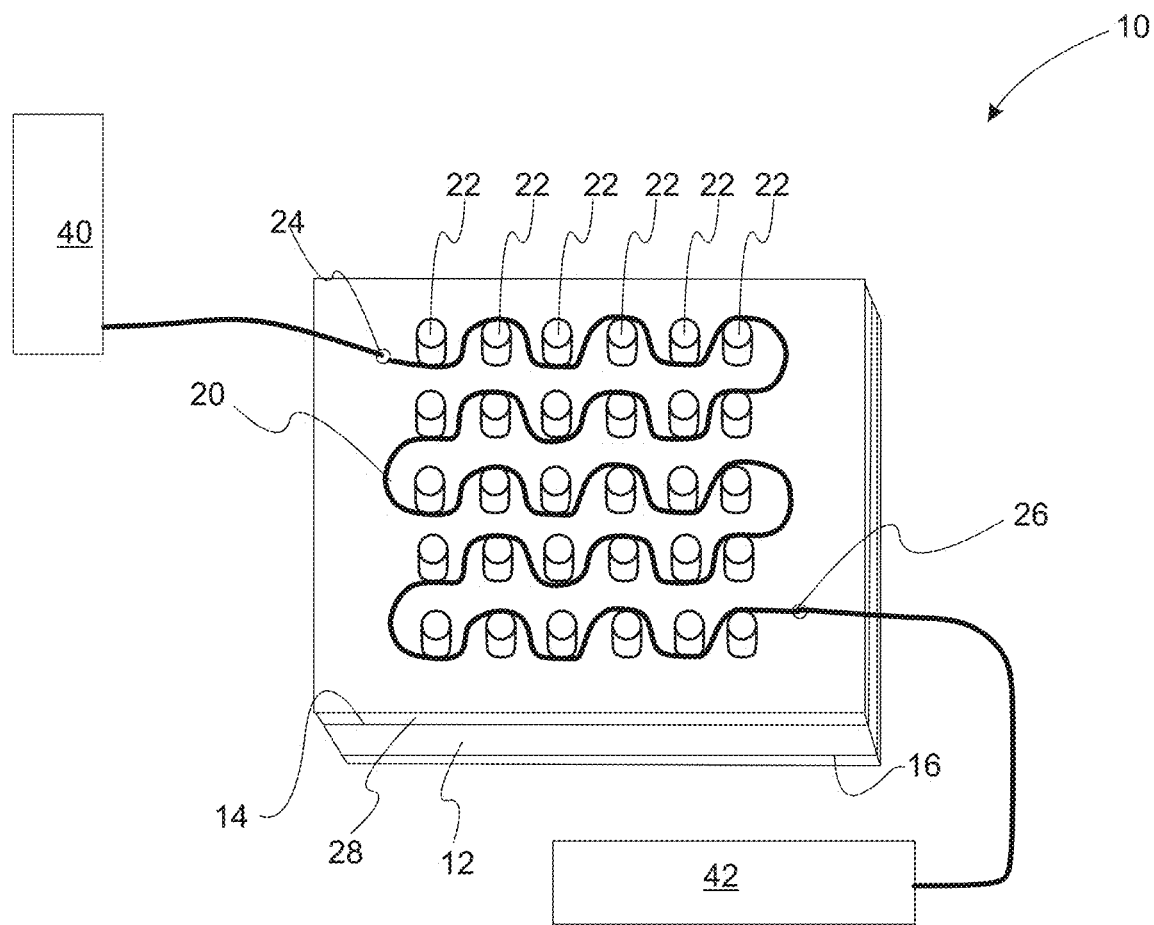
FIG. 2A. Schematic of an organoid Bioreactor.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

When referring to a numerical quantity, in a refinement, the term "less than" includes a lower non-included limit that is 5 percent of the number indicated after "less than." A lower non-includes limit means that the numerical quantity being described is greater than the value indicated as a lower non-included limited. For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, 1 percent, or 0 percent of the number indicated after "less than."

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For any device described herein, linear dimensions and angles can be constructed with plus or minus 50 percent of the values indicated rounded to or truncated to two significant figures of the value provided in the examples. In a refinement, linear dimensions and angles can be constructed with plus or minus 30 percent of the values indicated rounded to or truncated to two significant figures of the value provided in the examples. In another refinement, linear dimensions and angles can be constructed with plus or minus 10 percent of the values indicated rounded to or truncated to two significant figures of the value provided in the examples.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

The term "microfluidic" means that a device has a channel or structure with a dimension (e.g., width) on the order of a micron (e.g., equal to or greater than 1 micron and less than 1 millimeter).

The term "millifluidic" means that a device has a channel or structure with a dimension (e.g., width) on the order of a millimeter (e.g., equal to or greater than 1 millimeter and less than 10 millimeters).

The term "micro-millifluidic" means that a device has a channel or structure with a dimension (e.g., width) on the order of a micron (e.g., equal to or greater than 1 micron and less than 1 millimeter) and a channel or structure with a dimension (e.g., width) on the order of a millimeter (e.g., equal to or greater than 1 millimeter and less than 10 millimeters).

Throughout this application, where publications are referenced, the disclosures of these publications in their entireties are hereby incorporated by reference into this application to more fully describe the state of the art to which this invention pertains.

Figure 2B:
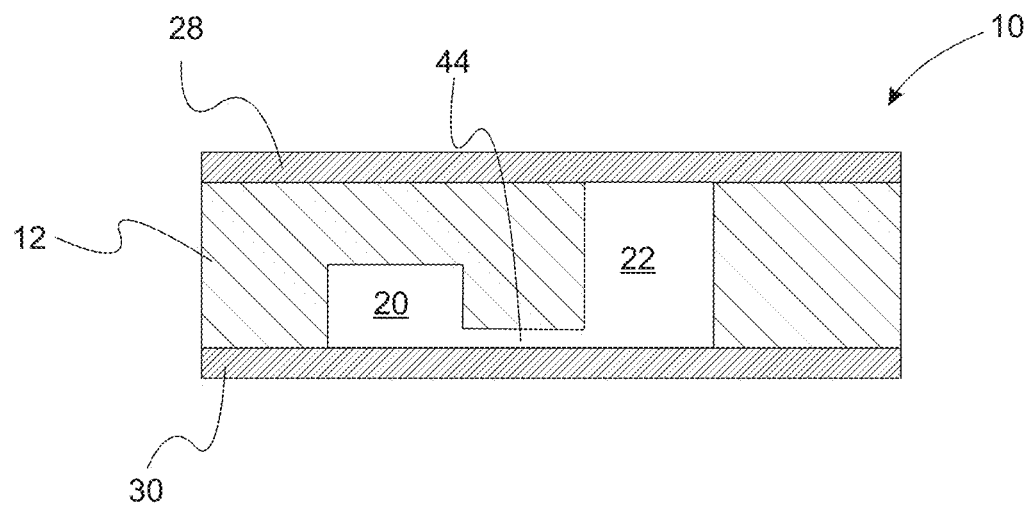
FIG. 2B. Schematic of a portion of an organoid Bioreactor.
Figure 2C:
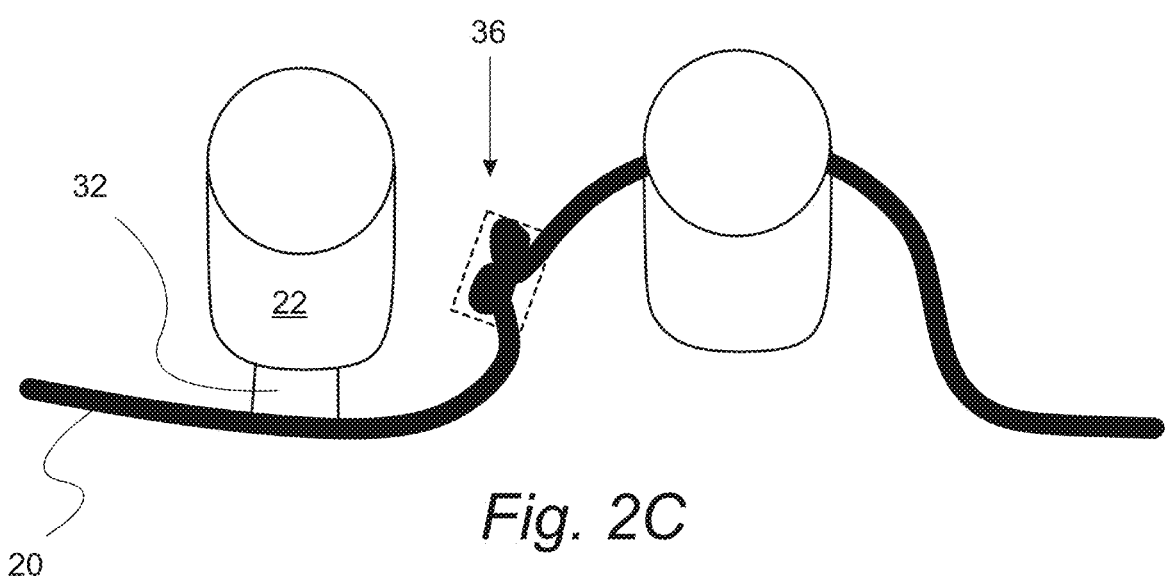
FIG. 2C. Schematic of a mixer between two adjacent chambers in the bioreactor organoid.

With reference to FIGS. 2A, 2B, and 2C, schematics of a bioreactor device are provided. Bioreactor device 10 includes a solid substrate 12 having a first face 14 and a second face 16. In a refinement, the solid substrate is composed of a moldable polymer (e.g., polydimethylsiloxane). The solid substrate at least partially defines a perfusion channel 20, a plurality of chambers 22, a fluidic inlet 24, and a fluidic outlet 26. A first sheet 28 is disposed over the first face and a second sheet disposed over the second face. Characteristically, the combination of the solid substrate 12, the first sheet 28 and the second sheet 30 define the perfusion channel 20 and each chamber 22 of the plurality of chambers. Characteristically, the perfusion channel 20 defines a serpentine path from the fluidic inlet section 24 to the fluidic outlet section 26. The plurality of chambers 22 are arranged in rows of chambers in which adjacent chambers are positioned at opposite sides of the perfusion channel 20. The perfusion channel 20 extends from the fluidic inlet 24 and the fluidic outlet 26 haves a serpentine path along each row of chambers. each chamber being in fluid. Each chamber is in fluid communication with the perfusion channel 20 through connecting channel 32 associated with each chamber 20. In some refinement, perfusion channel 20 has a height from 150-300 μm, and each chamber 22 has a height from 2-7 mm.

Still referring to FIGS. 2A, 2B, and 2C, bioreactor device 10 further includes a mixer 36 disposed between adjacent chambers. In a refinement, mixer 36 defines a tortuous path for fluid flowing therethrough.

Still referring to FIGS. 2A, 2B, and 2C, the first sheet 28 and the second sheet 30 are typically each independently transparent to wavelengths of light for performing spectral analysis or imaging or microscopy. In a refinement, the first sheet and the second sheet are each independently transparent to wavelengths of light for multiphoton imaging. In a further refinement, the first sheet and the second sheet are each independently transparent to wavelengths of light for fluorescence microscopy.

Still referring to FIGS. 2A, 2B, and 2C, bioreactor device 10 typically includes a media reservoir 40 in fluid communication with the fluid inlet 24 and/or a pumping device in fluid communication with the fluid outlet 26 for drawing fluid through the perfusion channel 42.

Referring to FIG. 2B, each chamber 22 has an associated connecting channel 44 that provides fluid communication between each chamber and the perfusion channel. Advantageously, each associated connecting channel 42 defines a distance from the perfusion channel 20 each associated chamber that eliminates fluidic movement in each chamber and reduces shear stress to allow for long-term culturing of organoids.

In a variation, the solid substrate is composed of a moldable polymer. An example of a moldable polymer is polydimethylsiloxane. Therefore, the solid substrate 12 can be fabricated by 3D printing a mold template for the solid substrate. Characteristically, the mold template having open template regions corresponding to solid substrate regions in the solid substrate and sold template regions corresponding to open substrate regions in the solid substrate. A liquid polymer precursor is poured over the mold template such that the open template regions are filled with liquid polymer precursor. The liquid polymer precursor in the mold template is cured. Finally, the solid substrate from the mold template.

In another variation, a method for culturing organoids using the bioreactor device set forth herein, and in particular retinal organoids, is provided. The method includes a step of placing an organoid in one or more of the chambers of the bioreactor device of claim 1, providing a culture medium to the plurality of chambers.

Figure 2D:
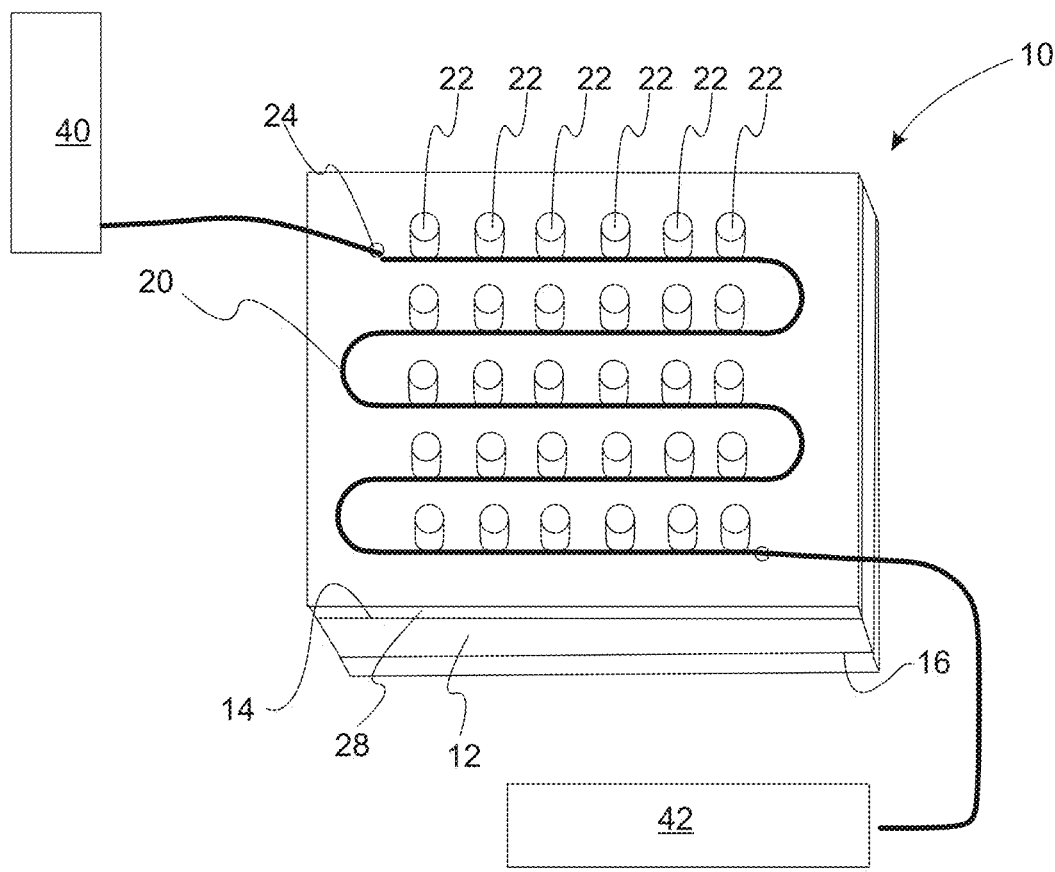
FIG. 2D. Schematic of an organoid Bioreactor.

With reference to FIG. 2D, another bioreactor device is schematically illustrated. Bioreactor device 10' includes a solid substrate 12 having a first face 14 and a second face 16. In a refinement, the solid substrate is composed of a moldable polymer (e.g., polydimethylsiloxane). The solid substrate at least partially defines a perfusion channel 20, a plurality of chambers 22, a fluidic inlet 24, and a fluidic outlet 26. A first sheet 28 is disposed over the first face and a second sheet is disposed over the second face. Characteristically, the combination of the solid substrate 12, the first sheet 28 and the second sheet 30 define the perfusion channel 20 and each chamber 22 of the plurality of chambers. The plurality of chambers are arranged in rows of chambers in which adjacent chambers in each row are positioned on the same side of the perfusion channel with chambers on adjacent rows are positioned on opposite sides of the perfusion channel 20. Characteristically, perfusion channel 20 extending from the fluidic inlet 24 to the fluidic outlet 26. Each chamber 22 is in fluid communication with the perfusion channel. A plurality of optional mixers 36 as set forth above, are positioned in the perfusion channel wherein at least one mixer is disposed between adjacent chambers.

The following examples illustrate the various embodiments of the present invention. Those skilled in the art will recognize many variations that are within the spirit of the present invention and scope of the claims.

I. METHODS

A. COMSOL Simulation

The simulation was performed using finite element analysis software, COMSOL Multiphysics (COMSOL, Inc, Palo Alto, CA, USA). COMSOL was used to evaluate different solid substrate designs and flow channel configurations to optimize mass-transport dynamics in culture chambers with different heights. Three major factors that affected the mass transfer rate were taken into consideration: 1) channel width (1000 or 500 μm wide), 2) channel configuration relative to culture chambers (linear single-sided chambers, serpentine alternating side chambers, serpentine with integrated mixer) and 3) the culture chamber height (2 or 4 mm tall).

The simulation parameters are listed in Table 1. The initial concentration of the whole system was set to zero, which was considered the most extreme condition. The left end of the channel was set as the inlet with concentration of 1 mol/m³ as the boundary condition.

TABLE 1

| Simulation parameters | |
|---|---|
| Physics | Laminar flow & Transport of diluted species |
| Study type | Time dependent |
| Material | Water |
| Diffusion coefficient (m²/s) | 6.00E−10 |
| Boundary conditions (mol/m³) | $c_{initial} = 0$, $c_{inlet} = 1$ |

B. Solid Substrate Design and Fabrication

The mold was designed using SolidWorks (SolidWorks Corp., Waltham, MA, USA) and the final design used for RtOg culture had the dimensions shown in FIG. 3A with channel height of 200 μm and chamber height of 2 mm. The chambers were arranged in a 6×5 array with the distance between each chamber at 9 mm, which was the same as that of a 96-well plate for compatibility with subsequent imaging steps. The mold was produced with 25 μm resolution with the Formlabs Form 3B printer (Formlabs, Somerville, MA, USA) using standard clear resin (Formlabs) (FIG. 3B). After printing, the mold was cleaned with 90% isopropanol to remove any resin residue. The mold was then air dried for 24 hours and cured with ultraviolet light for 30 minutes.

The bioreactor was fabricated from the printed mold similar to the molding steps in soft lithography[42]. Polydimethylsiloxane (PDMS) Sylgard 184 (Dow Corning, Midland, MI, USA) was mixed manually for 10 minutes at a 10:1 ratio (base elastomer/curing agent). After degassing in a vacuum chamber, the PDMS was poured over the 3D-printed mold until the level reached the top of the culture chamber features and degassed again in a vacuum desiccator to remove bubbles (FIG. 3C). After 48 hours of curing under room temperature, the molded PDMS piece was carefully peeled off from the mold. The fluidic inlet and outlet were created with a biopsy punch. Finally, the PDMS piece was treated with air plasma (Harrick) (Harrick Plasma, Ithaca, NY, USA) for 1 min. to promote adhesion and then pressure-bonded to a cover slip (#1.5, 64*50 mm, ClariTex) (Ted Pella, Inc., Redding, CA, USA) (FIG. 3D).

C. Stem Cell Culture and Retinal Organoids Initiation

Retinal organoids were differentiated from genetically modified NIH-registered cell line H9 human embryonic stem cells (hESCs) with green fluorescent protein (GFP) tagged to CRX gene which encodes cone-rod homeobox protein and is specifically expressed in photoreceptor cells[43-45]. Stem cells were maintained by feeding mTeSR 1 media (STEMCELL Technologies, Vancouver, BC, Canada) daily and passaged every 4-7 days by ReLeSR (STEMCELL Technologies) when cells reached ~80% confluency. Cells were expanded on Vitronectin XF™ (STEMCELL Technologies) coated plates at 37° C. in a humidified 5% $CO_2$ incubator (Nuaire, Plymouth, MN, USA).

To initiate organoid formation, Accutase (Nacalai Inc, Kyoto, Japan) was added to the stem cells into a single cell suspension when 2-dimensional culture reached ~80% confluency. The cells were then placed in an 800-μm micro-well EZSPHERE 12-well plate (Nacalai USA, Inc., San Diego, CA, USA) and centrifuged at 100 g for 3 min. to evenly distribute the stem cells throughout the bottom of each well. From day 1 to 7, the stem cells self-aggregated into embryonic bodies (EBs) in the EZSPHERE microwells. From day 8, the EBs were seeded onto a 1% growth factor reduced Matrigel (Corning, Corning, NY, USA) coated culture dish. The EBs spread onto the Matrigel and began 2D differentiation. Retinal eye fields were cut from the Matrigel between day 38 and 50 and transferred to ultra-low attachment 24-well plates (Corning Costar) (Corning, Corning, NY, USA) for 3D culture to be loaded into the bioreactor chip. Media used for retinal organoid differentiation was modified from Zhong et al.[46] From day 0 to 18, the organoids were gradually transitioned from mTeSR1 medium into neural induction media (NIM) containing Dulbecco's modified eagle medium (DMEM)/F12 (1:1) (Gibco, Waltham, MA, USA), 1% N2 supplement (Gibco), 1×minimum essential media non-essential amino acids (NEAA) (Gibco), 1×L-glutamine (Gibco), and 2 µg/ml heparin (Sigma-Aldrich, St. Louis, MO, USA), with daily media changes. From day 19 to 41, the media was switched to NIM containing DMEM/F12 (1:1) supplemented with 2% B27 supplement (50×) (minus vitamin A, Gibco), 1×NEAA, 1x L-glutamine, and 2 mg/ml heparin. From day 42 and beyond, the organoids were cultured with media containing DMEM/F12 (1:1) supplemented with 2% B27 Plus Supplement (50X) (Gibco), 1x NEAA, 1x L-glutamine, 2 ug/ml heparin, 100 µM taurine (Sigma), and 10% fetal bovine serum (FBS; Gibco). The media was changed 3 times a week and the organoids were maintained at 37° C. in a humidified 5% $CO_2$ incubator.

On day 41, 87, and 128 of differentiation, 12-15 RtOgs were randomly selected to load one each into every other chamber in the bioreactor chip. After about one month (30~37 days) of on-chip culture, RtOgs were used for histology, single-cell RNA sequencing. Same tests for the same age RtOgs in static culture group were performed. The detailed information of experimental groups was summarized in Table 1.

A second stem cell line was applied in these experiments. The hESCs (cell line CSC14, NIH registration no. 0284; AIVITA Biomedical, Inc) were maintained on Matrigel coated flasks and cultured in a xeno-free custom formulated media supplemented with low levels of bFGF and Activin-A (Peprotech, Rocky Hill, NJ, USA). Media was replaced daily, and flasks kept in a 37° C., 5% $CO_2$ tissue culture incubator. Every 4-5 days, colonies were passaged by enzymatic dissociation using collagenase IV (Gibco, 2 mg/ml) and transferred to a fresh Matrigel coated TC flask.

To initiate differentiation, growth factors are omitted, and media is replaced with a serum-free composition containing a GMP manufactured basal media, and Vitamin-A free B27 supplement (Gibco). Stem colonies are enzymatically released with collagenase IV (2 mg/mL) and aggregates allowed to form embryoid bodies (EB) for seven days in ultra-low adherence flasks. After seven days, EBs were transferred to Matrigel coated dishes and allowed to attach. Culture continues for 21 to 36 days with media replacement every 2-3 days. When refringent annular structures showing visible laminated morphology appear in the culture, these are the retina organoids to dissect and place in suspension culture. At day 55 of 3D culture, media is changed to B27 with Vitamin A (Gibco) and 10% (v/v) fetal bovine serum (Gibco) for long term culture. Retina organoids are fed every 2-3 days until needed.

Ten RtOgs on day 70 of differentiation were randomly selected and cultured on the chip for a month (35 days) until day 105. The organoids were divided into two groups for gene expression qPCR analysis afterwards. The same tests were performed for RtOgs in the static culture group.

D. Bioreactor System Assembly and Organoid Loading

The chip and the associated tubing were disinfected with 70% ethanol and 30 min. in a UV and ozone cool clave (CoolCLAVE Plus) (Genlantis, San Diego, CA, USA). Each chamber was treated with anti-cell adherence solution twice (STEMCELL Technology) and washed by Dulbecco's phosphate-buffered saline (DPBS) without calcium and magnesium (STEMCELL Technology). The on-chip culturing system was assembled as shown in FIG. 3F. The media reservoir was comprised of a 50 mL Steriflip-GP sterile centrifuge tube (MilliporeSigma, Burlington, MA, USA) and a filter cap with a pore size of 0.22 µm.

Before loading the organoids, the chip chambers were sealed by pasting a slice of MicroAmp™ optical adhesive film (Thermo Fisher Scientific, Waltham, MA, USA) on the top surface. Then the syringe was slowly withdrawn to apply negative pressure to fill the channel with fresh media drawn from the media reservoir. Tubing clamps were then applied to block both the inlet and outlet tubing, so that the adhesive film could be removed without disturbing the fresh media level in the channel. One organoid was loaded into each chamber by 20 µL pipette tips with tips cut off. Lastly, the top of the chambers was resealed with sterile optical adhesive film (FIG. 3E). The flow rate used for long-term culture was 250 µL/h. Under this flow rate, 50 mL media was sufficient for about 8 days of culture. When changing the media, the inlet and outlet tubing were clamped, and fresh media was refilled in the centrifuge tube. All these steps were performed in an ESCO Class II Type A2 biosafety cabinet (Labculture, ESCO) (ESCO Micro Pte. Ltd., Singapore) to avoid contamination.

E. In Vitro Dye Test

The dye test experiment was performed to compare the uniformity of the concentration in chambers between the four different channel designs. Four chips with 3×3 chamber array were fabricated with 2-mm chamber height. The channels were first filled with blue food dye solution following similar steps as the organoid loading procedure (FIG. 3E). The flow was then blocked by clamping both the inlet and outlet tubing, and the inlet was switched to a yellow dye solution. Lastly, a syringe pump was used to draw the yellow dye solution into the chip at a rate of 600 µL/h. The whole flow process was recorded with a camera. The grayscale value of each chamber was obtained by ImageJ to quantify concentration changes of each chamber from the images.

F. Fluorescence Life-Time Imaging

Figure 10A:
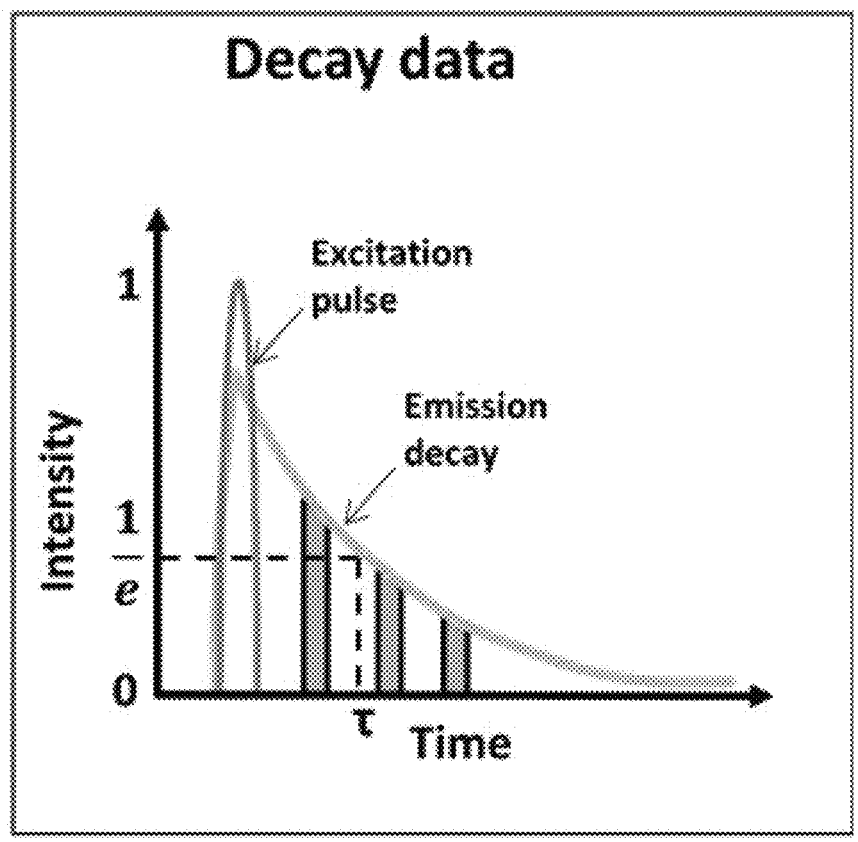
FIGS. 10A, 10B, and 10C. Fluorescence lifetime imaging and analysis using the phasor approach. (A) Fluorescence lifetime was acquired by quantifying emitted fluorescent photon over time after an excitation pulse was supplied to obtain an emission decay curve; (B) Phasor plot produced a 2-dimensional space for intrinsic fluorophors with different lifetimes corresponding with different types of metabolism (oxidative phosphorylation favors bound NADH and glycolysis favors free NADH) and different amounts of oxidative stress (long lifetime species). The free/bound NADH ratio and long LLS ratio were obtained by calculating projecting the 3 dimensional photon count histogram onto the Bound-Free axis and LLS axis respectively; (C) A representative images of RtOg analyzed by the phasor approach. The autofluorescence images encapsulated all total fluorescence, while the f/b NADH and LLS are pseudo color images based on the phasor analysis of quantized fluorescent emission. f/b NADH was free to bound NADH ratio. LLS was long lifetime species.
Figure 10B:
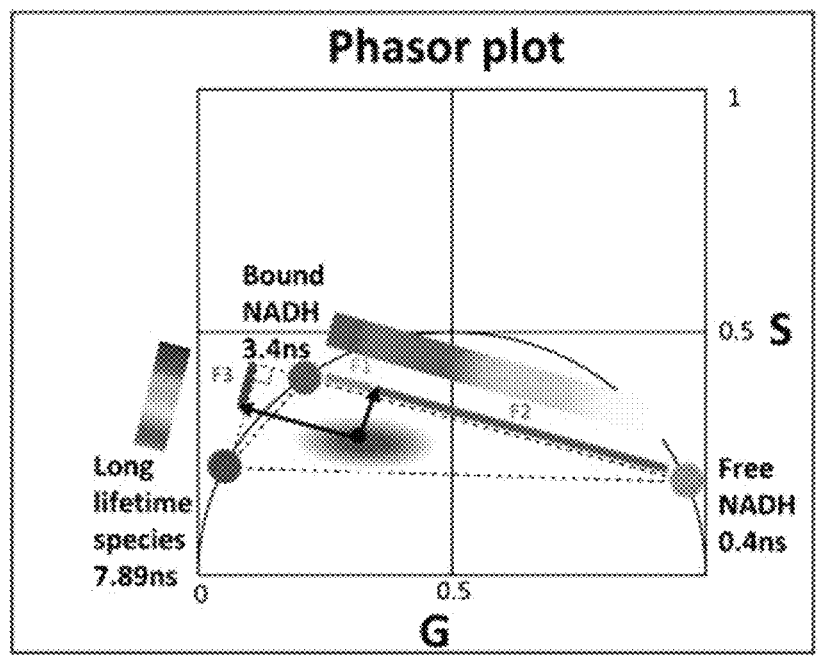

Fluorescence lifetime imaging (FLIM) was used to study the intrinsic fluorophore Nicotinamide adenine dinucleotide (NADH) in the RtOg. The fluorophore's emission decay curve was obtained by photon counting to calculate the fluorescent lifetime (FIG. 10A). FLIM data was displayed on a phasor plot after Fourier transform, with the intensity decay curve of fluorescence for each pixel represented by the g and s coordinates. Using this method, the decay and spectrum for each pixel could be depicted on the phasor plot (FIG. 10B).

Figure 10C:
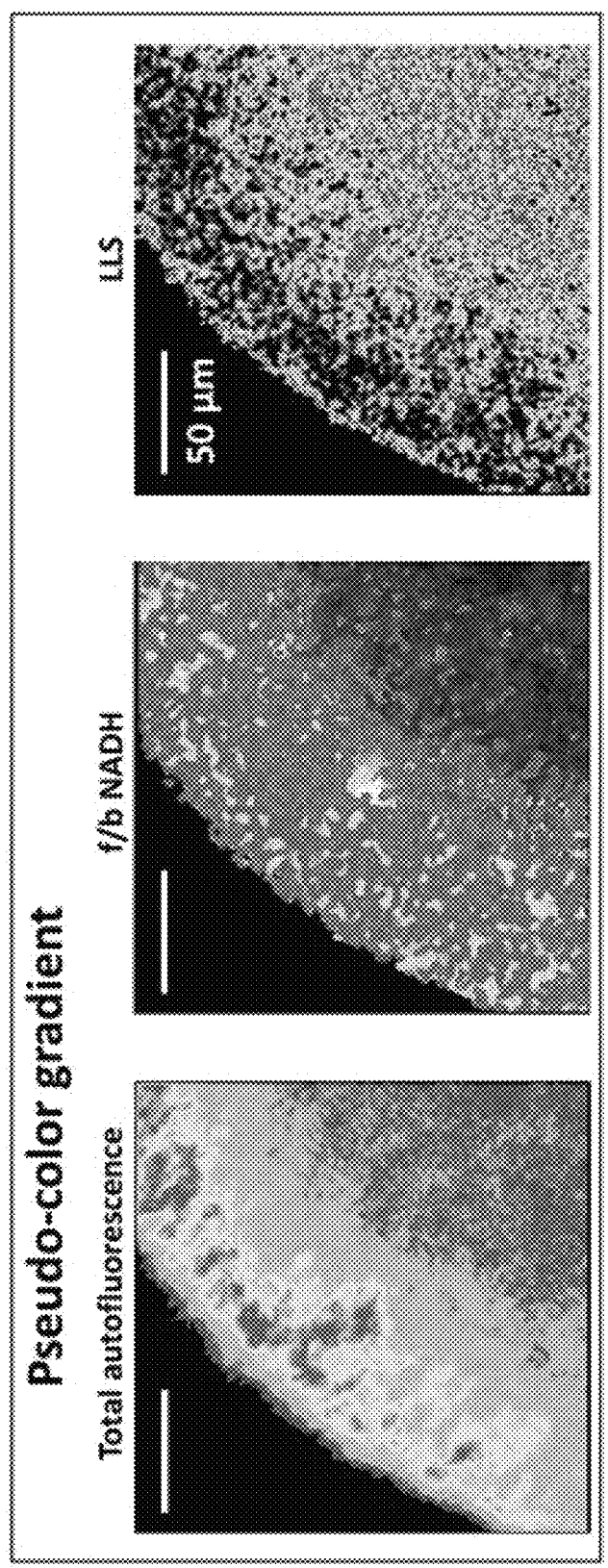
Figures 12A, 12B, 12C, 12D:
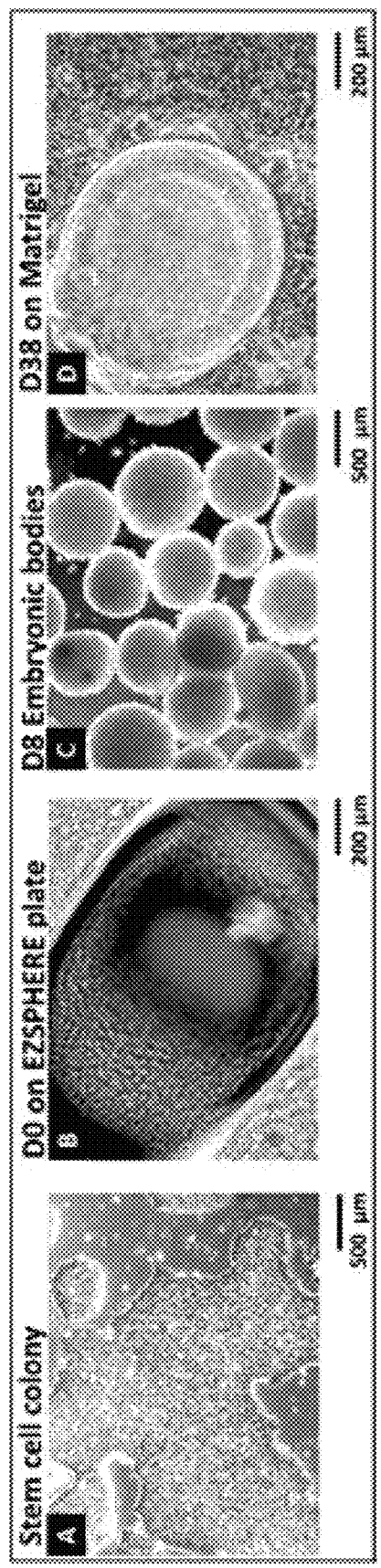

The metabolic trajectory was visualized using the phasor approach[47]. The phasor plot has a universal circle, with boundaries of each point representing a single exponential lifetime of one type of molecule. Different components on the phasor plot followed a linear relationship, thus, the ratio of the linear combination could be used to determine the fraction of each component. The lifetime of free and lactate dehydrogenase-bound NADH was about 0.37 ns and 3.4 ns, respectively[48]. Free NADH was linked to more glycolysis and a more proliferative state, while bound NADH was correlated with more oxidative phosphorylation and a more differentiated state[49]. The lifetime of lipid was 7.89 ns associated with long lifetime species (LLS) (FIG. 10B), the presence of which indicated oxidative stress[50]. The fraction of each component was calculated as FIG. 10B suggested, F1/F2 was the free/bound NADH ratio, and F3 was the ratio of LLS. Based on the above mechanism, the metabolic state of RtOgs was quantitatively evaluated by calculating the free/bound NADH ratio and LLS ratio in representative image cross-sections. Qualitatively, the metabolic differences were visualized by applying a pseudo color gradient to the phasor plot (FIG. 10C).

Images were taken by a Zeiss LSM 780 microscope using a Plan-Apochromat 20x/0.8 M27 objective (Carl Zeiss, Jena, Germany). The excitation wavelength was 740 nm, produced by Mai Tai multi-photon laser source (Spectra-Physics Mai Tai, Mountain View, CA). Imaging settings used were as follow: 256×256 frame size, 1.66 µm pixel size, 25.21 µs pixel dwell time and 8-bit pixel depth. Emission laser passed through an MBS 690+ and an SBS SP 610 filters and the lifetime data was collected by the photomultiplier tube (H7422p-40, Hamamatsu, Japan) and a320 FastFLIM FLIMbox (ISS, Champaign, IL). Before imaging, the system was calibrated on frequency factor and lifetime by coumarin 6 solution with the known lifetime of 2.5 ns. FLIM data were collected after 100 counts in the brightest pixel of the image were acquired. During imaging, fresh medium flowed into the bioreactor continuously, while RtOgs in static groups were moved into Nunc® Lab-Tek® II Chambered Coverglass (Thermo Fisher) for imaging.

G. Phase Contrast Imaging

The phase contrast microscopy images were acquired using an Olympus IX71 (Olympus, Tokyo, Japan) and a QICAM FAST1394 CCD camera (Teledyne Qlmaging, Surrey, BC, Canada) under two magnifications by UPlanFL N 4×/0.13 PhL and UPlanFI 10×/0.30 PhL objectives.

H. Green Fluorescent Protein Imaging

Green fluorescent protein images were acquired using a Zeiss LSM 780 microscope using Plan-Apochromat 20×/0.8 M27 objective (Carl Zeiss, Jena, Germany). The excitation wavelength was 488 nm with a pixel dwell time of 1.58 µs. A frame size of 512×512 pixels was used with each pixel being 0.42 µm.

I. Quantitative Polymerase Chain Reaction Analysis

The primers for qPCR test are listed in Table 2 (Qiagen, Germantown, MD, USA). 12 retinal progenitor and photoreceptor genes was used with 1 housekeeping gene to identify and quantify the gene expression profile in retinal organoids. Human adult retinal tissue was used as a positive control (n=3). For CRX-GFP hESCs derived RtOgs, each sample was analyzed on days 122 to 124 of differentiation (n=3 for both static and chip groups); for CSC14 hESCs differentiated RtOgs, each sample was analyzed on day 105 (n=2 for both static and chip groups). Each sample consisted of 4 RtOgs. Trizol reagent (Qiagen), DNase I digestion (Invitrogen, TURBO, Waltham, MA, USA), and phenol-chloroform extraction (Fisher) were used to isolate RNA, and an $RT^2$ cDNA synthesis kit (Qiagen) was used to synthesize cDNA. $RT^2$ SYBR Green with ROX qPCR master mix (Qiagen) was used for amplification, which was performed under the following conditions: 95° C. (15 minutes), 40 cycles at 95° C. (15 seconds each), 55° C. (30 seconds each) and 72° C. (30 seconds each). The annealing temperature was 60° C. The double delta cycle threshold (Ct) method was used to calculate the fold expression, and day 0 undifferentiated hESC (line CSC14) was used as a control. For analysis and heatmap generation, non-detected amplification in the control tissue and organoids were assigned cycle threshold values of 40. Heat maps were generated using Graphpad Prism software (Graphpad Software LLC, La Jolla, CA, USA), the heat map has the value of $\log_2$(Fold Expression).

J. Single Cell Dissociation

Eight to twelve RtOgs on day 72 and 159 (chip vs. static, four experimental groups in total) were dissociated using papain-based enzymatic digestion by Worthington papain dissociation system (Worthington, Lakewood, NJ, USA), followed the standard dissociation protocol provided by Worthington. Briefly, the papain vial was dissolved in 5 mL of EBSS buffer in 37° C. water bath for 10 minutes to yield a solution at 20 units of papain per ml in 1 mM L-cysteine with 0.5 mM EDTA. After adding 250 µl DNase (2000 units/ml deoxyribonuclease in EBSS) into the papain solution. The RtOgs were added in the papain solution and incubated at 37° C. incubator on a rocker platform for 1 hour. Post incubation, the tissue was further triturated using 18G needle and syringe. The dissociated tissue mixture was centrifuged at 300 g for 5 minutes at room temperature. After removing the supernatant, the cells were resuspended in the albumin-inhibitor solution with 2.7 ml EBSS, 150 DNase and 300 µl ovomucoid solution (10 mg/ml Egg White/BSA in EBSS). The single-cell solution was then carefully layered on top of 5 ml albumin-inhibitor solution and centrifuged at 70 g for 6 minutes at room temperature. The supernatant of dead cells was discarded, and the pelleted cells were immediately resuspended in 1% BSA/PBS solution. The cell viability was tested by 0.4% trypan blue using a hemocytometer (>90%) and the concentration was adjusted to ~870 live cells/ul. The samples were sent for scRNA-seq library preparation within 5 minutes.

K. Single-Cell RNA-Seq Library Preparation

Sequencing libraries were prepared using the protocol from 10X Genomics Chromium Single Cell 3' Reagent Kit v3.1 (10X Genomics, Pleasanton CA). Briefly, the 10X workflow was followed using 10,000 cells as the capture target. The resulting Gel-in-Emulsions (GEMs) were transferred to PCR tubes and incubated in a Bio-Rad C1000 Thermocycler (Bio-Rad Laboratories, Hercules, CA) for the reverse transcription protocol. The GEMs were cleaned up using Dynabeads MyOne SILANE (Life Technologies, Carlsbad CA) and then amplified using 11 cycles according the 10X workflow. The cDNA was cleaned using 0.6X SPRIselect (Beckman Coulter, Indianapolis, IN) size selection and then quality control assays using Qubit DNA HS assay (Life Technologies, Carlsbad CA) and Agilent 2100 Bioanalyzer DNA HS (Agilent, Santa Clara, CA) were performed. The endogenous cDNA fraction was then processed according to the 10X workflow for library construction. The cDNA was fragmented, end repaired and then A-tailed. After a SPRIselect cleanup the adapters were ligated on the cDNA. Sample indexes were added by PCR and a double-sided size selection using SPRIselect was performed. The libraries were assayed for quality using Qubit DNA HS assay, Agilent 2100 Bioanalyzer and quantified by Kapa qPCR Library (Roche, Basel, Switzerland) quantification for Illumina platform. The libraries were sequenced in the Illumina NovaSeq 6000 (Illumina, San Diego, CA) using 28 cycles for read 1, 8 cycles for the index read and 100 cycles for read 2.

L. Single-Cell RNA-Seq Data Analysis

Raw reads were first subjected to quality control QC analysis with FASTQC software and aligned to the reference transcriptome Grch38 using a short-read aligner STAR68 through the 10X pipeline software cellRanger v.3.1.0. Gene level expression for each valid cell was then quantified using UMI (Unique Molecular Identifier) and normalization was performed. Dimension reduction was then used to visualize and explore major features in single cell RNA-seq data. PCA, t-distributed Stochastic Neighbor Embedding (t-NSE) and UMAP was performed using cellRanger followed by unsupervised clustering methods such as K mean clustering to identify sub populations and cell types in the sample.

Loupe browser v.5.0.1 was then used to visualize the further explore marker gene expression.

M. Immunohistology

RtOgs were fixed with cold 4% paraformaldehyde in 0.1M Na-phosphate buffer for 1 hour, cryoprotected (30% sucrose) and frozen in optimum cutting temperature (OCT) compound (PolarStat Plus, StatLab, McKinney, TX, USA). Organoids were then cryo-sectioned into 10 µm serial sections and stored at −20° C. Histo-VT One (Nacalai) was used for antigen retrieval at 70° C. Primary and secondary antibodies used are listed in Table 3. Organoid sections were incubated in primary antibody dilutions at the concentrations listed overnight at 4° C. The following day, sections were left incubating in primaries at room temperature for an hour before washing. Sections were then incubated at room temperature for at least 30 minutes in fluorescent secondary antibodies. Following 30 minutes of incubation in 4,6-diamidino-2-phenylindole (DAPI) at a concentration of 50 µg/ml, slides were coverslipped using Vectashield Vibrance Antifade Mounting Medium (Vector Labs, Burlingame, CA, USA).

Fluorescent sections were imaged using a Zeiss LSM700 confocal microscope (Zeiss, Oberkochen, Germany). Tiled stacks of 5-8 µm thickness were taken at 20X and 40×magnifications. Images were extracted using the Zen 3.3 Software (Zeiss). Regions of interest for cell counting were outlined in Adobe Photoshop software (San Jose, CA, USA). Cell counting was performed using ImageJ Software (U.S. NIH).

N. SEM & TEM Sample Preparation and Imaging

Samples were fixed in Karnovsky's fixative (2% Paraformaldehyde/2.5% Glutaraldehyde in 0.2 M sodium cacodylate buffer) and stored at 4° C. overnight. The tissue was then washed by 0.1 M cacodylate buffer and post fixed in the solution (1:1 mixture of 0.1 M cacodylate buffer: 0.2 M cacodylate buffered 2% osmium tetroxide) for 2 hours on ice. The tissue was dehydrated in 35%, 50%, 70%, and 95% ETOH for 15 minutes each.

The organoids were cut into halves in 100% ETOH and washed again with 100% ETOH. Starting from this step, half of each organoid was prepared for SEM and the other half was used for TEM. For TEM samples, after two changes of propylene oxide (15 minutes each), the tissue was then infiltrated in a 1:1 mixture of propylene oxide:Epon Araldite resin overnight. The next morning, this mixture was changed out to fresh Epon Araldite for 2 hours. The sample was then placed into flat embedding molds and polymerized at 60° C. for 48 hours. The resin blocks were then cut by Leica EM UC7/FC7 cryo-ultramicrotome (Leica, Wetzlar, Germany). The TEM used in this study was JEOL 2100 (JEOL USA Inc, Pleasanton, CA, USA). The montages were processed by the program Etomo (University of Colorado, Boulder).

For SEM samples, the organoids samples were processed by a Leica critical point dryer. The surface of the sample was sputter coated with platinum using a Leica ACE200 sputter coater before imaging. The SEM used in this study was FEI Magellan 400 XHR (FEI Company, Fremont, CA, USA) with an Everhart-Thornley detector (ETD) and a Through-the-Lens detector (TLD).

O. Statistical Analysis

Data in the plot were presented as means with standard deviations. Graphpad Prism software was used for all statistical analyses. In the GFP MFI, immunohistology cell count, free/bound NADH and LLS ratio figures, one-way ANOVA tests were performed. In the qPCR heatmap, two-way ANOVA tests were performed. The significance was determined by a p value less than 0.05.

I. RESULTS

A. Microfluidics Design and Testing

The bioreactor chip was designed with the distance between chambers matching a 96-well plate to retain microscope compatibility. Preliminary designs in which chambers were located on one side of a 1000 µm wide perfusion channel revealed two problems: 1) heterogeneous media concentration changes between chambers and 2) low mass transfer efficiency (FIG. 11). Therefore, not all wells in the preliminary design received comparable fresh media exchange. To optimize the design and improve mass transfer rates, three different variables were evaluated with COMSOL simulation: channel width, channel alignment and chamber height.

The channel width determined the cross-section area and thus affected the flow velocity (v) as indicated in Equation (1). Holding volume flow rate (Q) constant, the larger the cross-sectional area (A), the slower the flow velocity (v) would be.

$$Q = Av \quad (1)$$

According to the definition of Péclet number ($Pe_L$, the ratio of advective transport rate to diffusive transport rate, Equation (2)), a larger flow rate would lead to a higher advective transport rate, accelerating mass transport.

$$Pe_L = \frac{Lv}{D} \quad (2)$$

where L is the characteristic length, v the local flow velocity, and D the mass diffusion coefficient. Therefore, narrowing the channel width would facilitate an increase in flow velocity. Based on the simulation results, under both flow rates, the narrow channel (500 µm) designs showed faster mass transfer (FIGS. 4A-B) and therefore, a theoretically faster delivery of media to each culture chamber.

Incompressible fluid flow within the microfluidic device, due to its small size, should be laminar with a parabolic velocity profile when fully developed. As a result, the velocity next to the channel walls should be close to zero. Thus, the designs with all chambers on one side of each channel should show a higher velocity in the fluid close to the channel wall connected to a chamber than the flow velocity on the opposite wall without a connected chamber. FIGS. 4A-B demonstrate that single-sided channel had a concentration gradient from the first chamber to the last chamber in each row and then entire series of chambers. This difference was even more pronounced in a larger series of 5×6 chambers (FIG. 11). To minimize this effect, a serpentine channel was designed to promote comparable media diffusion from both sides of the channel. To further improve concentration distribution, a mixer unit was added between each chamber[51]. Simulation demonstrated that narrow channels with or without mixer showed comparable qualitative performance as indicated with the color map representation of the concentration variations between the first and last culture chambers in each row and those between rows.

The third variable evaluated with simulation was the chamber height. By tracking the point concentration on the same top corner of each chamber, the 3D COMSOL simulation results showed that doubling the height of the chamber to 4 mm caused a dramatic change (4-10 folds difference) in mass transport efficiency (FIG. 4D). To maximize the transport efficiency, 2 mm was chosen as the final chamber height for bioreactor fabrication. FIG. 4E shows the 4D concentration patterns in four different bioreactor designs.

Figures 4F, 4G:
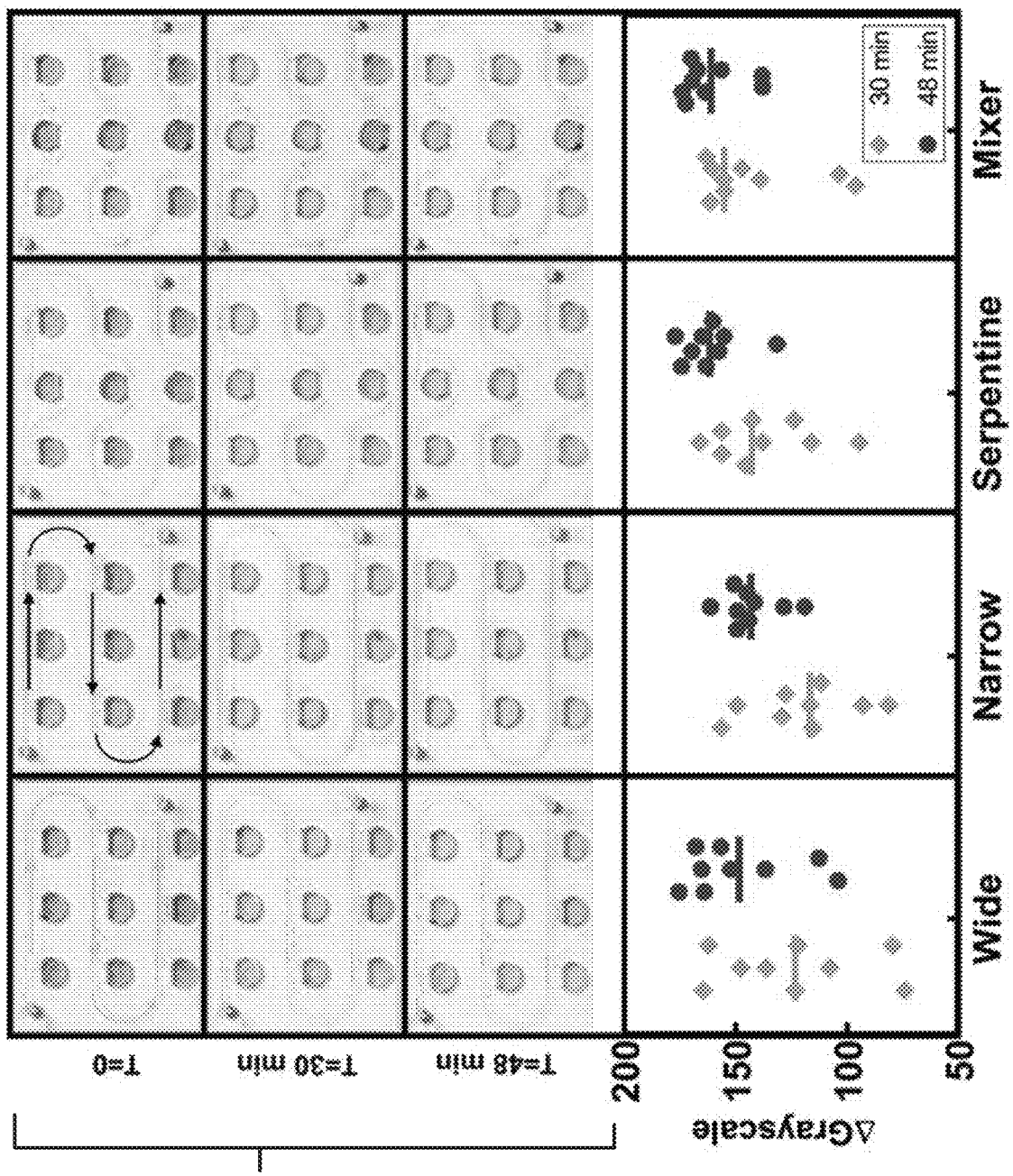

To confirm simulation results and examine the functionalities of the four designs, a dye test was performed to confirm the optimum design for culturing RtOgs. A 3×3 chamber array was fabricated for each channel design with a 2 mm tall culture chamber. Blue dye was used to fill each channel followed by 30 and 48 minutes of 600 µL/h flow of yellow dye (FIG. 4F). The grayscale photogrammetry from pictures taken on each chamber were quantified (FIG. 4G). The serpentine channel with mixer design showed the smallest standard deviation, indicating that this design had the most uniform concentration among the four. The serpentine channel without mixer exhibited the next best performance based on variability after 48 minutes of flow. The simple serpentine channel without an integrated mixer showed higher fabrication success with 3D printing and lower probability of trapped air bubbles in the microfluidic channels than the serpentine channels with mixer.

B. Retinal Organoid Culture Methods Comparison

Phase Contrast Imaging

Representative phase contrast images in FIGS. 12A-D showed the key stages of RtOg differentiation from human embryonic stem cells. The EZSPHERE microwell aggregated stem cells into uniformly sized embryonic bodies which were then plated on Matrigel coated dishes. Eye fields cut from Matrigel were maintained in ultra-low attachment 24-well plate as they assembled into RtOgs. In this study, RtOgs were put on the bioreactor on days 41, 87 and 128 of differentiation, respectively.

Figures 5A, 5B, 5C, 5D, 5E, 5F:
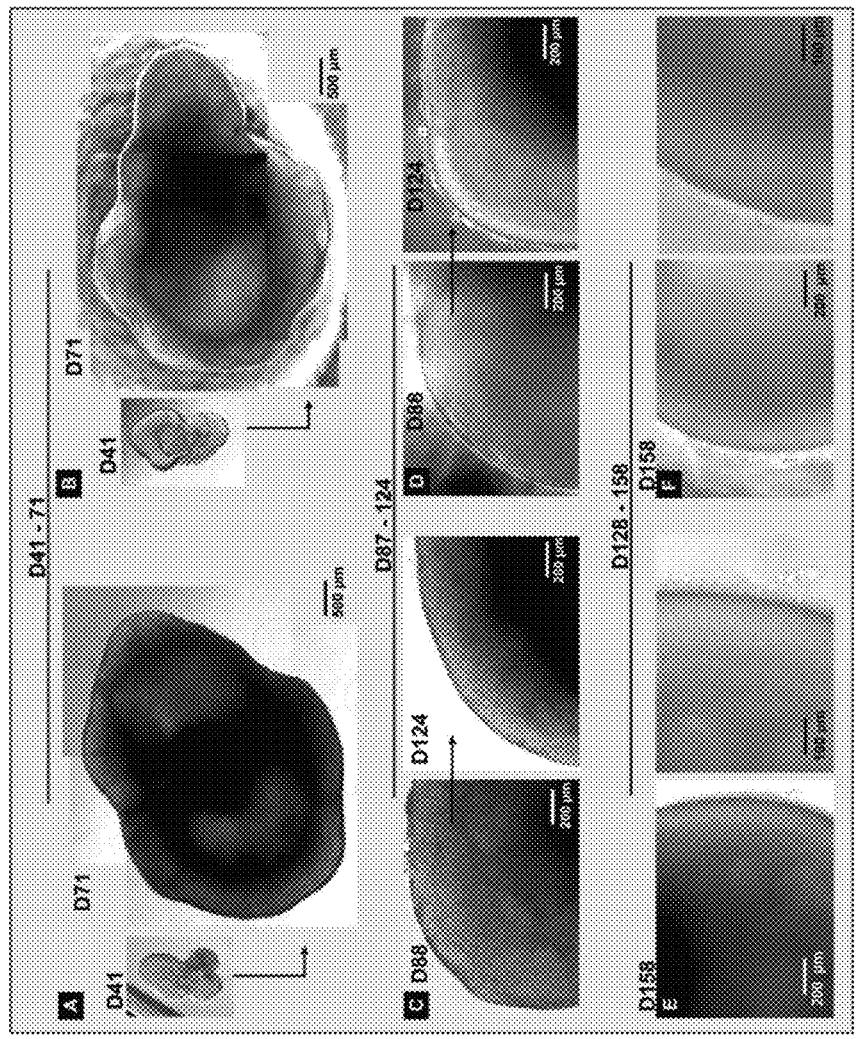
FIGS. 5A, 5B, 5C, 5D, 5E, and 5F. Representative phase contrast images of organoid differentiation in bioreactors and static culture during different stages of development. The same RtOg in static culture (A) and bioreactor culture (B) from day 41 to 71 demonstrating the magnitude of RtOg growth (Day 41 insets share the same 500 μm scale bar as Day 71 larger insets); (C) The same RtOg in static culture from day 88 to 124; (D) The same RtOg in bioreactor culture from day 88 to 124; (E-F) RtOgs on day 158 of differentiation showed outer segment structures in both static and bioreactor groups. (C-F) Higher magnification figures were shown on the right.

At an early differentiation stage from day 41 to day 71, RtOgs in both static and bioreactor groups showed a significant size change (FIGS. 5A-B) and developed hollow center and transparent edge. FIGS. 5C-D showed a representative RtOg in both groups on day 88 and day 124 of differentiation, respectively. The transparent and laminar outer surface, which was observed in both groups, indicated the development of photoreceptor layer. In later differentiation stages from day 128 to day 158, the RtOg's edge became more mature and developed outer segment-like structures on their surface (FIGS. 5E-F). Overall, there was no observable morphological difference between static and bioreactor cultured organoids.

Fluorescence Lifetime Imaging

The bioreactor chip platform was continuously supplied with nutrients while the RtOgs in conventional dish culture received nutrient exchanges every 3 days. FLIM was used to measure the metabolic activity in a non-invasive and non-destructive way as described in the method section.

Figure 6M:
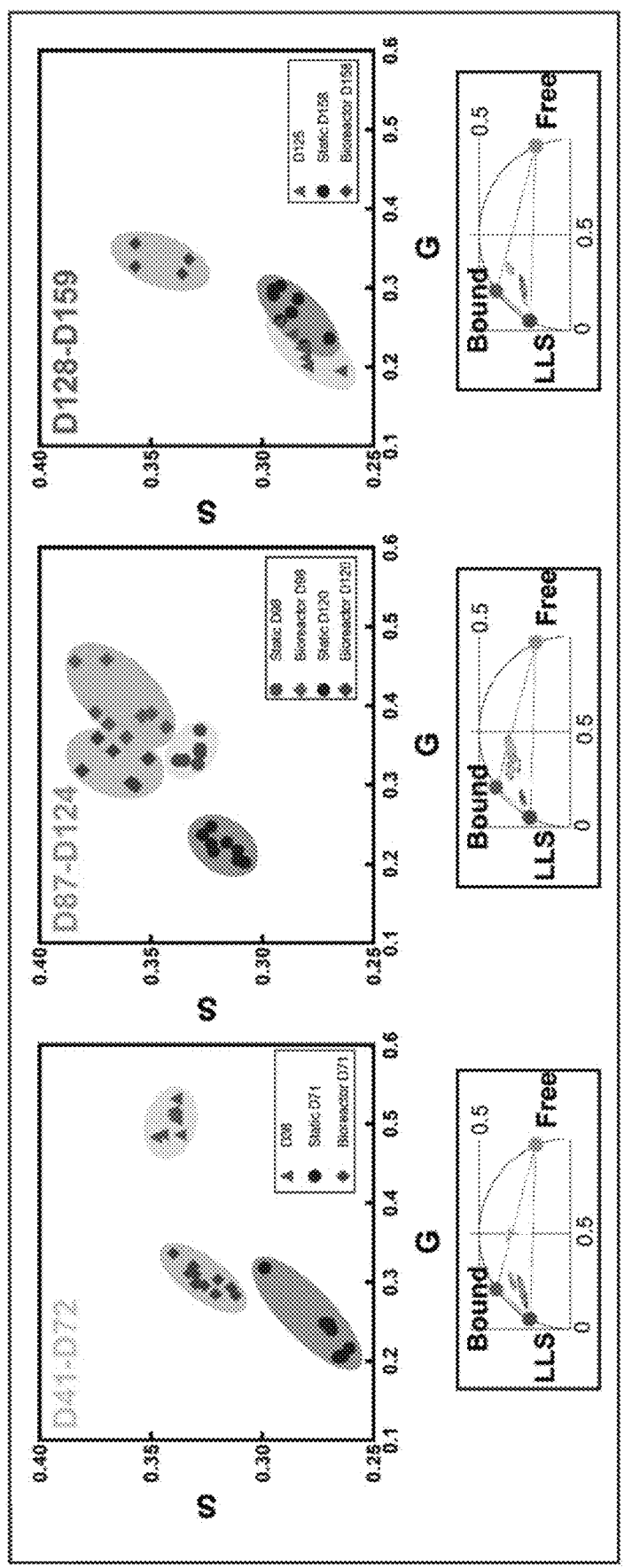

Four imaging modalities were used to visualize the same cross-section in RtOgs. Conventional fluorescence microscopy demonstrated green fluorescent protein (GFP) in photoreceptors and their progenitors in the CRX-GFP organoids (FIGS. 12A-D). Multiphoton infrared stimulation was used to acquire total autofluorescent images showing the total NADH (FIGS. 6A-D), which delineated cellular structures and viability of RtOgs. Multiphoton lifetime imaging revealed metabolic changes in NADH from its free to bound form and their associated free:bound ratio (f/b NADH) (FIGS. 6E-H). Long lifetime species analysis highlighted oxidative stresses in the tissues (FIGS. 6I-L). The above two values were calculated based on the location of the datapoints on the phasor plot (FIG. 6M).

RtOgs at different differentiation stages were imaged. For the D41-72 and D128-158 groups, RtOgs were imaged 3 days before the bioreactor and static comparison experimen started (D38 and D125). After approximately one month of culture under two conditions, RtOgs were imaged again at the endpoint (D71 and D158). For the D87-124 group, RtOgs were imaged at two time points (D98 and D120) during the culture period.

Figure 6O:
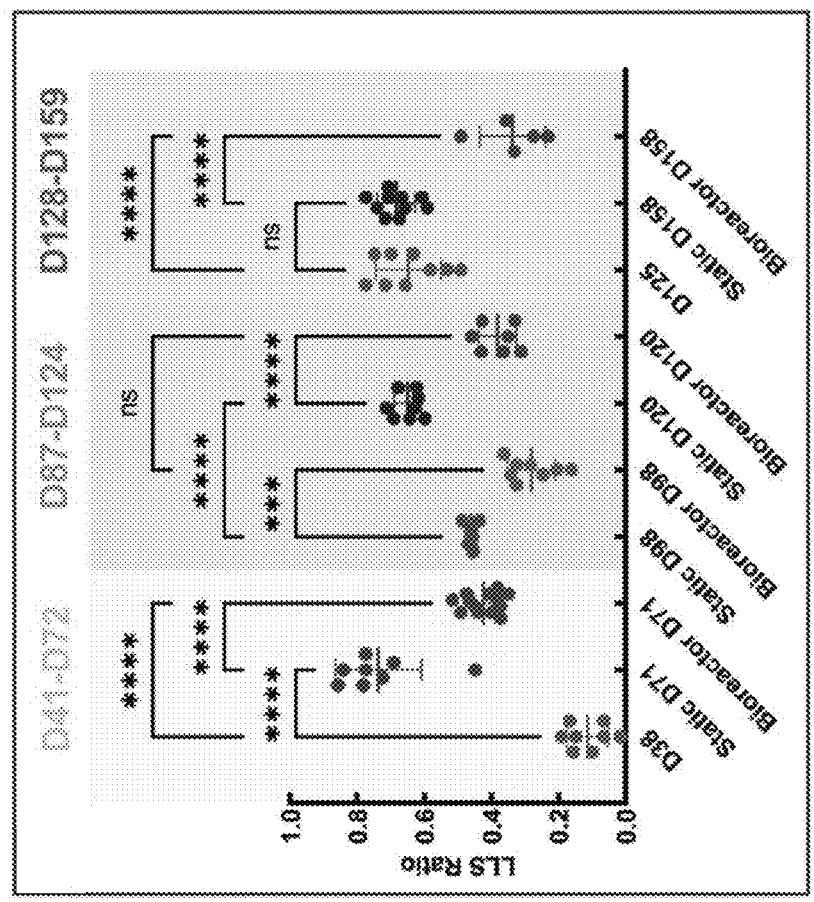
Figure 6N:
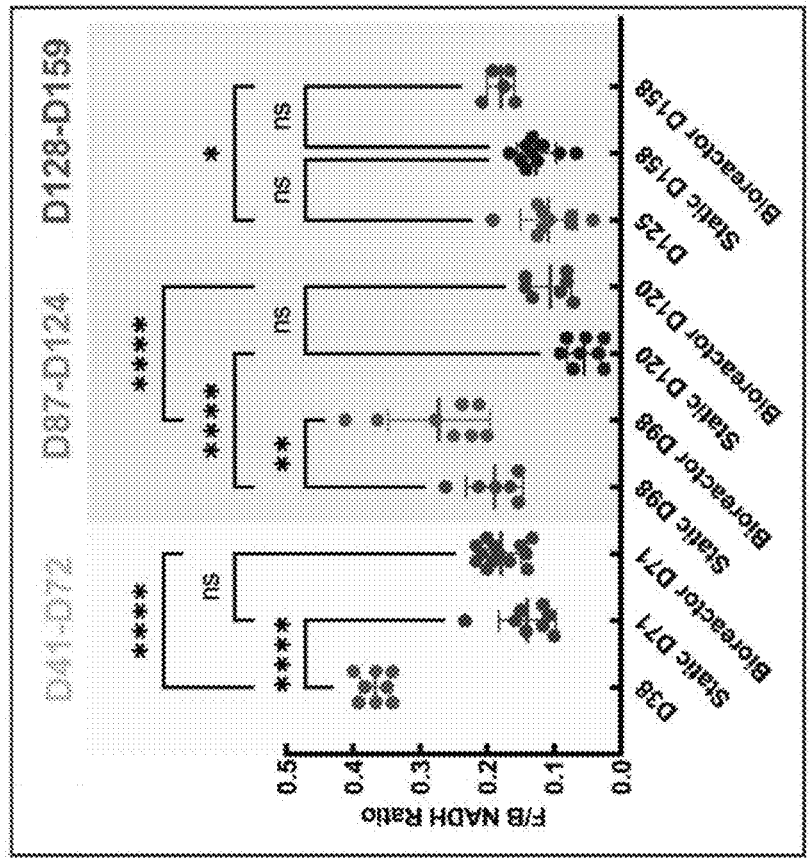

RtOg differentiation in both static and bioreactor groups demonstrated a shift from more glycolytic to more oxidative phosphorylated metabolism according to the f/b NADH ratio (FIG. 6N). On day 38 of differentiation the f/b ratio was the highest (FIG. 6N). The pseudo color-coded f/b NADH distribution from day 98 to day 120 of differentiation visualized the developmental trend from more glycolytic (yellow-green) to more oxidative phosphorylation (red) (FIGS. 6E-H). A higher total fluoscence NADH metabolic signature was present in bioreactor cultured organoids (Comparing FIGS. 6G and 6H). When comparing the f/b ratio of bioreactor and static culture RtOgs, no significant difference was identified in the f/b NADH ratio on day 71, 120 and 158 (FIG. 6N).

LLS is a marker for oxidative stress and RtOgs in both groups showed a significant increase of LLS ratio over time (FIG. 6O). RtOgs on the bioreactor experienced significantly lower LLS signatures on FLIM imaging than RtOgs in static culture at all imaged timepoints (FIG. 6O). False color LLS images showed a distinct color difference between two groups (FIGS. 6K-L). FIG. 6L highlights that the innermost layer (where progenitor cells, ganglion cells and Müller glia are located) of the static cultured organoid experienced a higher LLS signal (more red) than the bioreactor cutlured RtOgs. The outer layer (where photoreceptors are located) of static cultured RtOgs experienced lower LLS signal (more blue) than bioreactor cultured RtOgs. The time-dependent metabolic shifts and the metabolic difference between two groups were visualized on G-S phasor plot, which highlights the metbolic fingerprint of RtOgs before and after culture in static or bioreactor conditions. The G-S plot demosntrates differential clustering of RtOgs cultured under static or bioreactors conditions at 3 stages of differentiation (FIG. 6M).

Gene Expression Profile by Single-Cell RNA Sequencing and qPCR

Figures 7E, 7F, 7G:
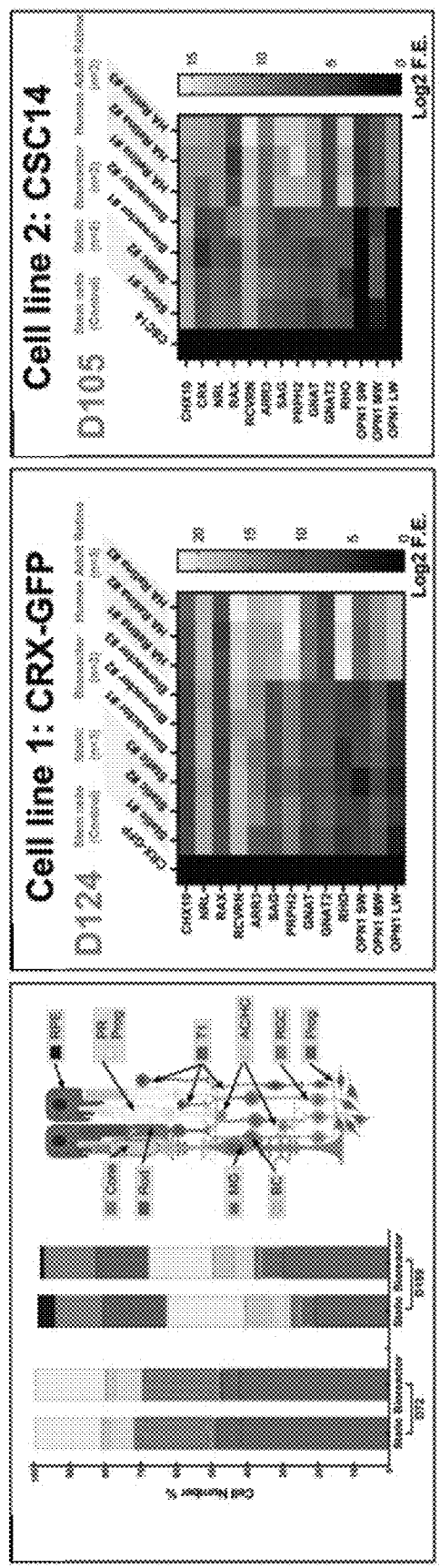

The gene expression profile of RtOgs at several stages of differentiation was focused on and compared their cellular profiles maintained in bioreactors and static culture condition. scRNA seq was used to study static- and bioreactor-cultured RtOgs on day 72 and day 159 of differentiation. The genes to distinguish and identify specific cell populations were previously described[52,53] (FIGS. 7A-D). qPCR analysis was performed for two different stem cell lines—CRX-GFP (day 124) and CSC-14 (day 105) (FIGS. 7F-G).

Single-cell RNA seq provided a comprehensive overview of cell types within RtOgs. RtOgs that had been maintained in either static culture or bioreactor culture for approximately 1 month were studied at two different time points: D72 and D159. For both static and bioreactor cultured RtOgs, the three predominant cell types on day 72 were retinal progenitor cells (Prog), retinal ganglion cells (RGC) and photoreceptor progenitor cells (PR Prog). Many cells were also in the transition phase 1 (T1) as identified by ATO7 (a marker cells differentiating from retinal progenitor cells to other cell types)[52,53](FIGS. 7A, C). The population difference of each cell type between static and bioreactor group on day 72 was very small (FIG. 7E).

Within mature RtOgs after 1 month of static or bioreactor culture on day 158, more advanced cell types emerged and formed more distinct clusters on the scRNA seq UMAP (FIGS. 7B, D). The percentage of RGC decreased, while the proportion of bipolar cells (BC) and Müller glia (MG) increased. PR progenitor cells further differentiated into rods and cones. Compared to static culture RtOgs, those in the bioreactor group contained a higher percentage of retinal progenitor cells. The bioreactor group showed a similar population of rods and cones, while static group RtOgs contained more rods. Both groups have differentiated cell types that corresponded to cell types found in vivo mature human retina.

Analysis using qPCR included a short list of retinal genes (detailed information in Table 2). RtOgs derived from CRX-GFP hESCs expressed retinal progenitor genes (CHX10, NRL and RAX) that were comparable to those of human adult retina in both static and bioreactor groups (FIG. 7F). Both groups also expressed rod and cone genes including RCVRN, ARR3, SAG, PRPH2, GNAT and GNAT2. However, both static and bioreactor cultured RtOgs showed low mature photoreceptor gene expression. Gene expression levels by qPCR were not significantly difference between the static and the bioreactor groups (two-way ANOVA test, p>0.05). Similar results were obtained from the CSC-14 hESCs derived RtOgs at 105 days of differentiation (FIG. 7G); there was no significant gene expression difference between static and bioreactor culture conditions (two-way ANOVA test, p>0.05).

Immunohistology and Electronic Microscopy

RtOgs maintained in both conventional static culture or the bioreactor for approximately 1 month were fixed on day 72 and 159 of differentiation. Cryostat sectioning was performed to acquire immunohistology images to visualize cell types and structures. On day 72 of differentiation, RtOgs in both groups demonstrated layered cellular structures (FIG. 8). The apical aspect was composed of photoreceptor progenitor cells, marked by orthodenticle homeobox 2 (OTX2), and retinal progenitor cells, which were immunoreactive for visual system homeobox 2 (CHX10/VSX2) (FIGS. 8A, C). The basal aspect contained amacrine cells which were immunoreactive for calretinin (CAL2) (FIGS. 8A, C). There were also some retinal ganglion cells marked by brain-specific homeobox/POU domain protein 3A (BRN3A, also known as POU4F1) (FIGS. 8B, D). The expression of synaptophysin (SYP) indicated synaptogenesis (FIGS. 8B, D).

Figures 9A, 9B, 9C:
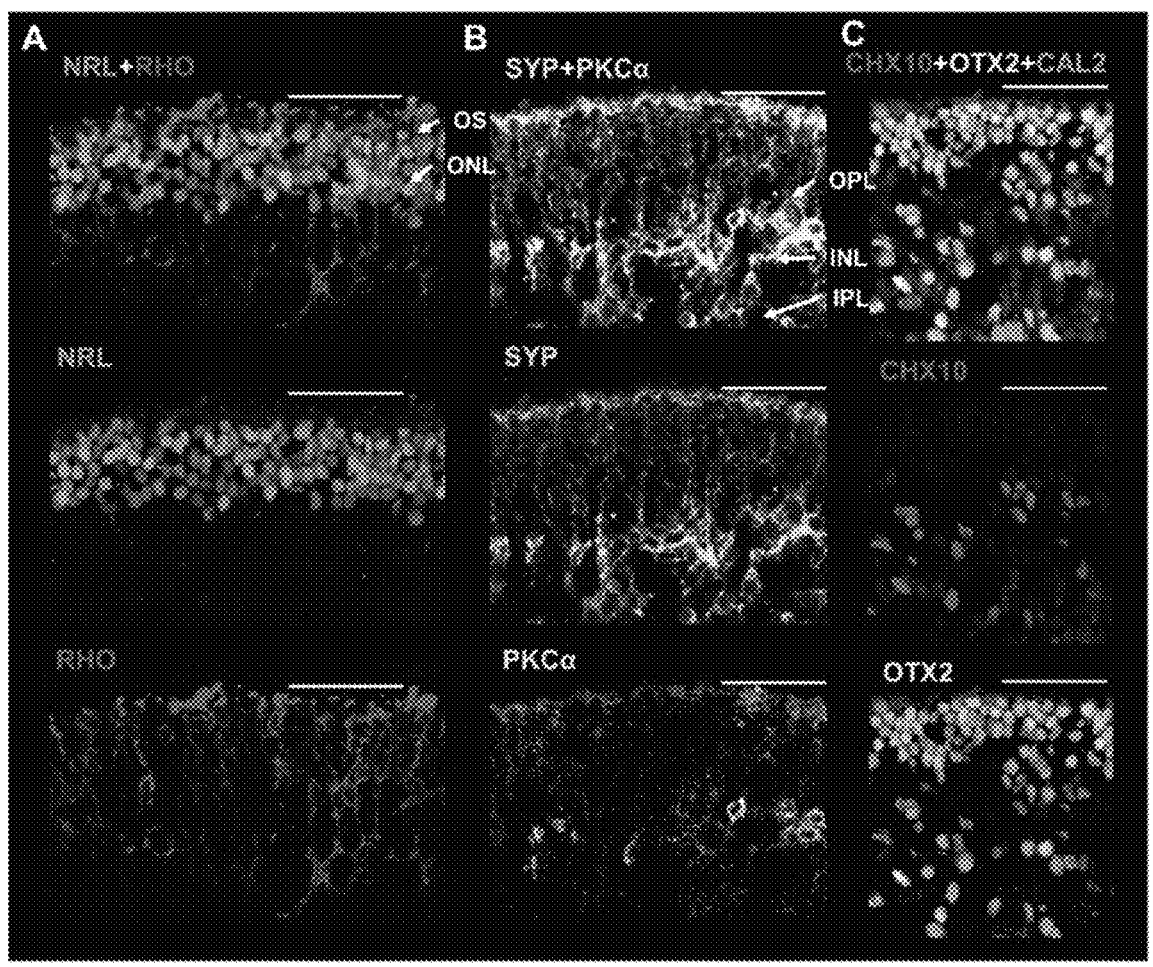
FIGS. 9A, 9B, 9C, 9D, 9E, 9F, 9G, 9H, and 9I. Immunohistology and SEM images of RtOgs on day 159 of differentiation. Immunostaining images of static (A-C) and bioreactor (D-F) cultured RtOgs. SEM images of static (G) and bioreactor (I) cultured RtOgs; (H) Cell counting from selected immunohistology slides (RCVRN+: nstatic=2, nbioreactor=3; RHO+: nstatic=3, nbioreactor=3; NRL+: nstatic=3, nbioreactor=3). Antibody marked cells: RHO—rod photoreceptors; NRL—photoreceptors; CHX10—retinal progenitor cells; OTX2—photoreceptor progenitor cells; CAL2—amacrine cells; SYP—synaptophysin; PKCα—rod bipolar cells. Arrow markers: OS—outer segment; IS—inner segment; CC—connection cilium. ONL—outer nuclear layer; OPL—outer plexiform layer; INL—inner nuclear layer; IPL—inner plexiform layer. (scale bar: 50 μm)
Figures 9D, 9E, 9F:
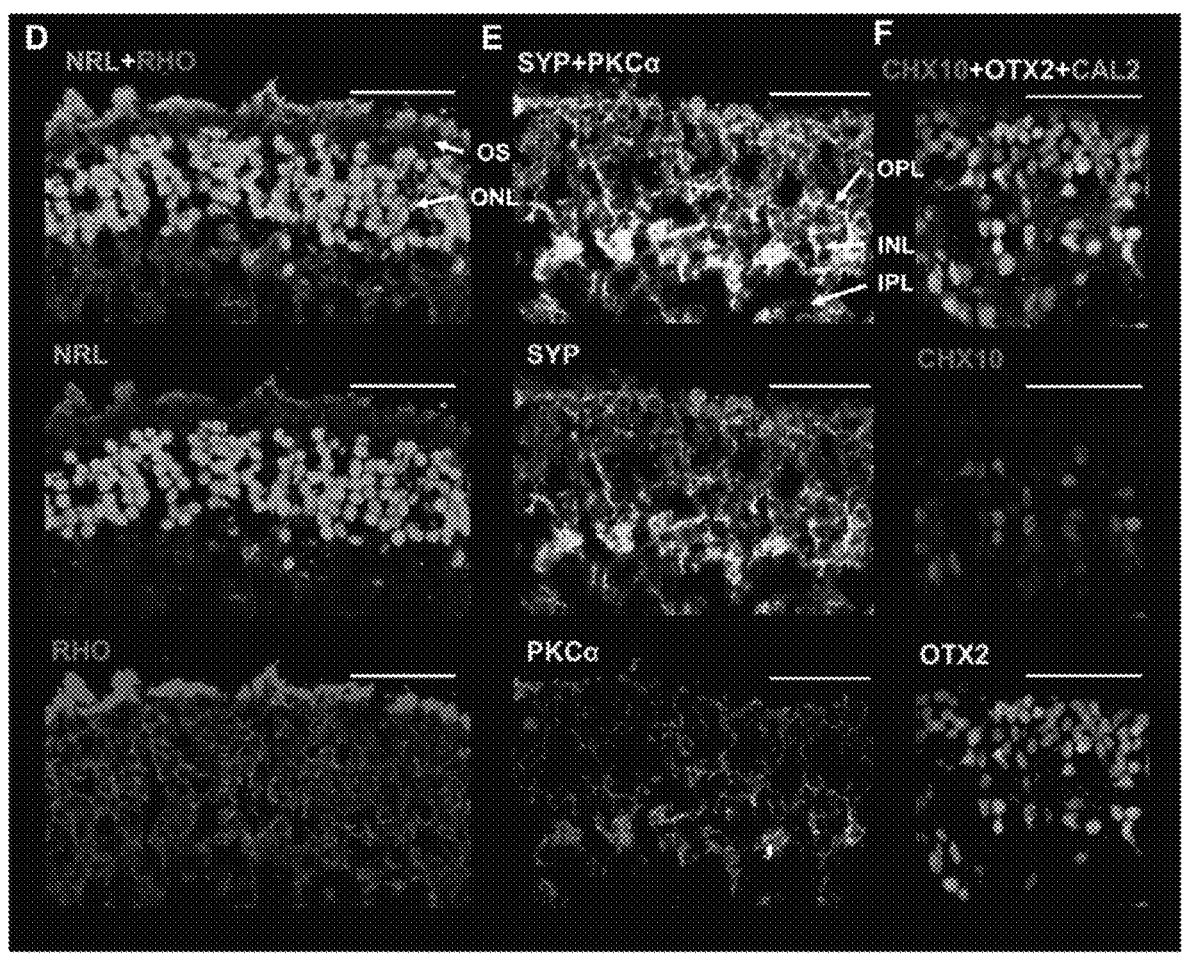
Figure 9G:
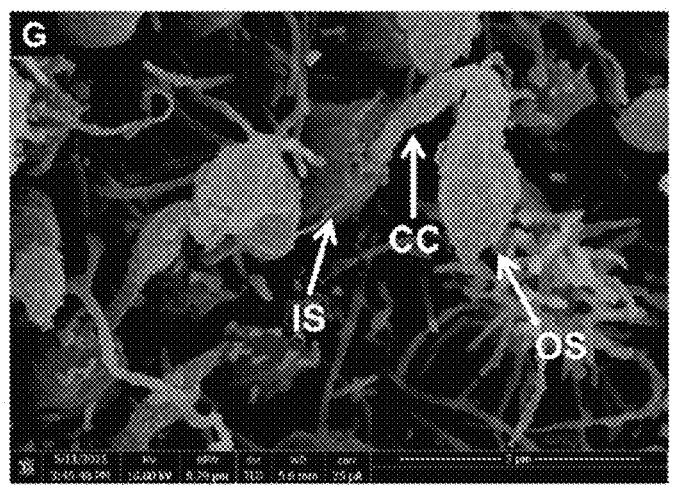
Figure 9H:
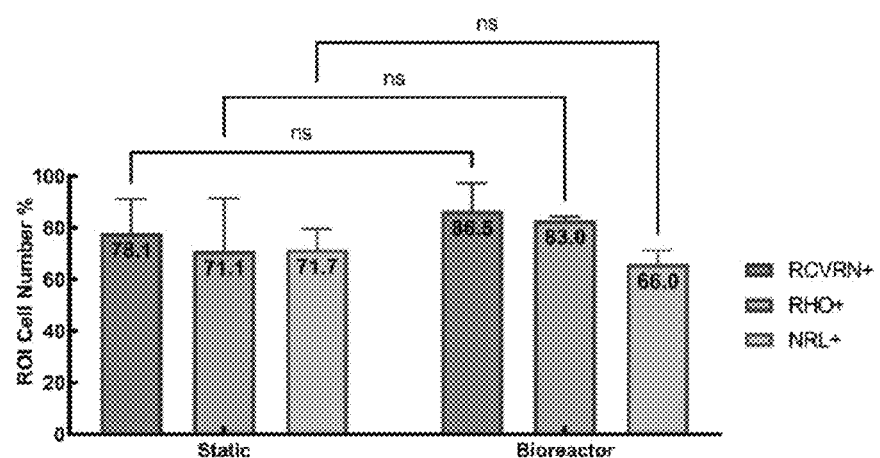
Figure 9I:
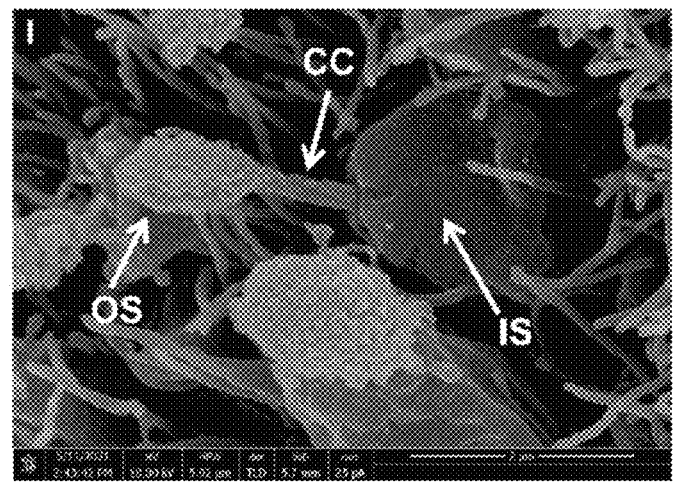
Figure 13:
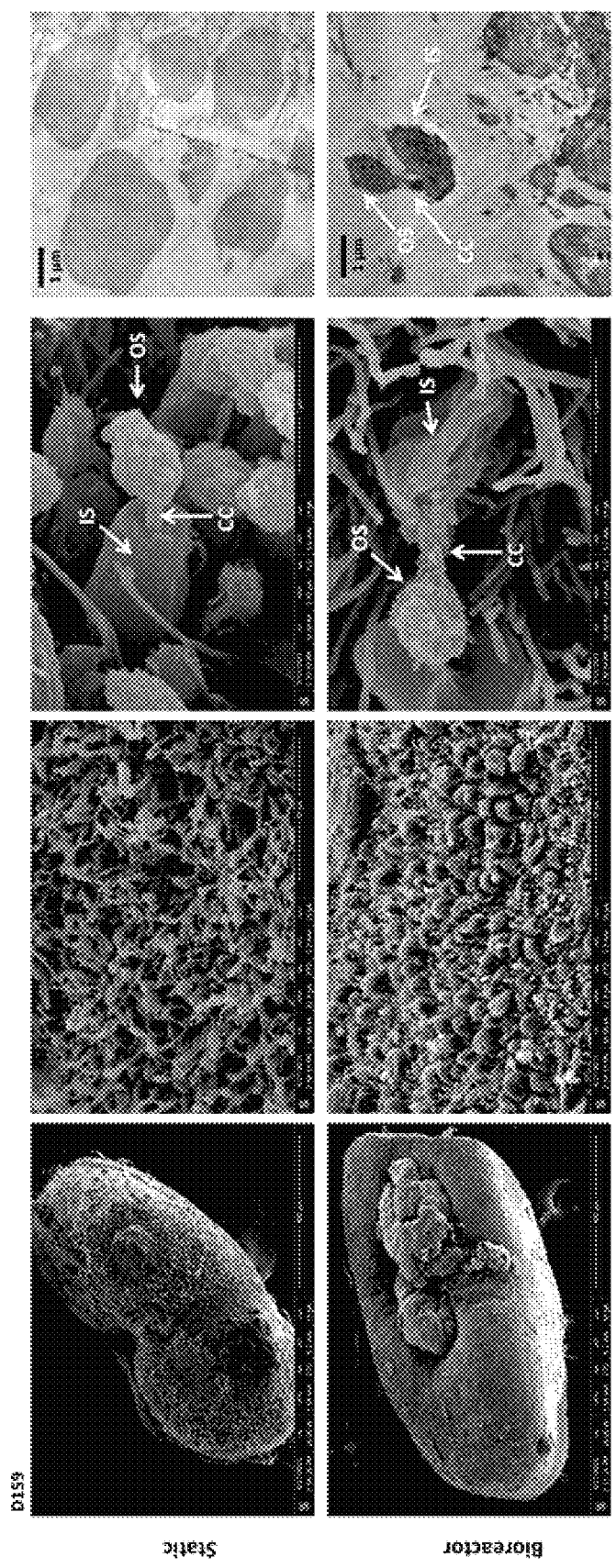
FIG. 13. SEM and TEM images of RtOgs on day 159 of differentiation showed outer segment-like structures. Arrow markers: IS—inner segment, OS—outer segment, CC—connecting cilium.
Figure 14:
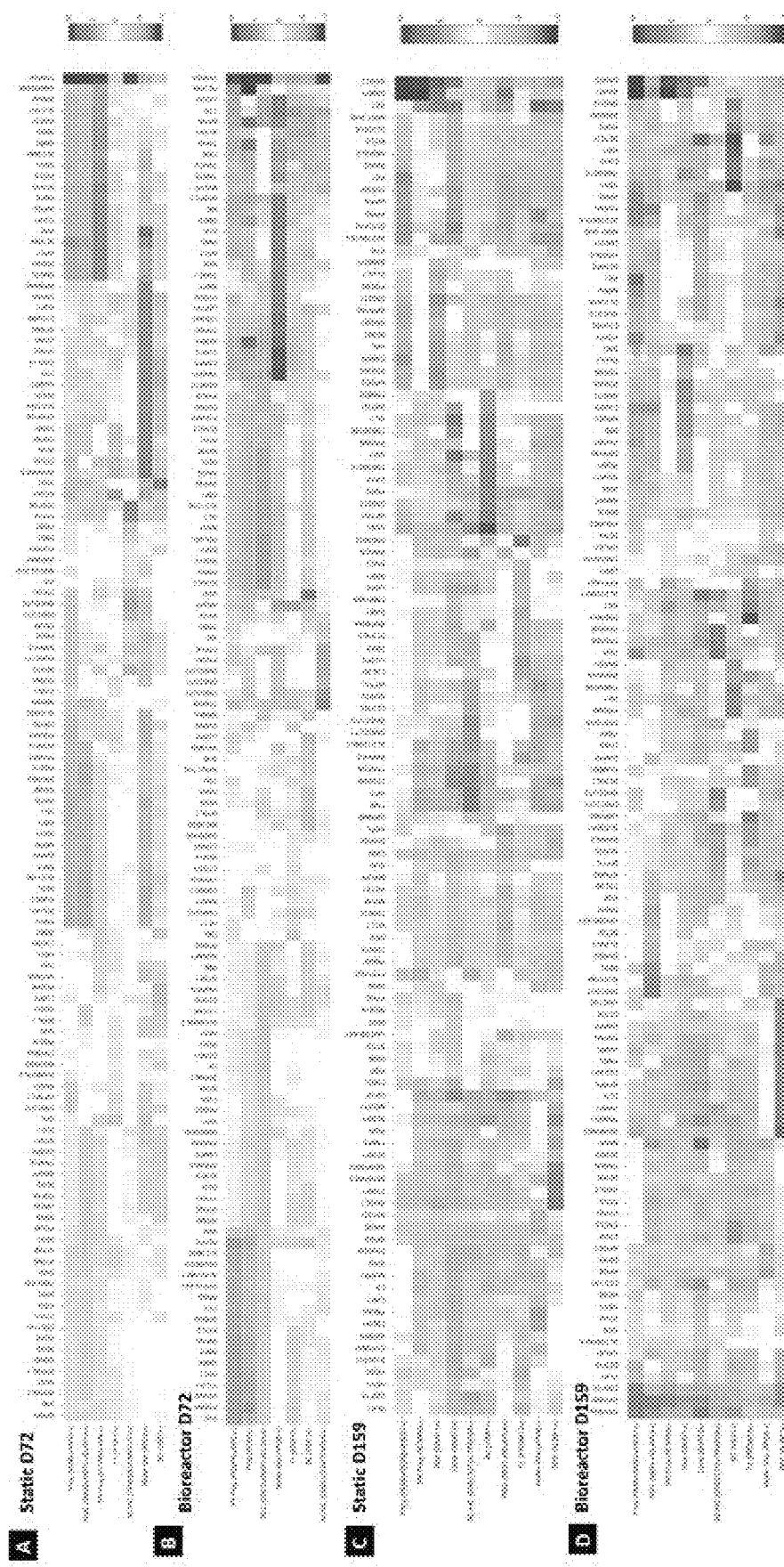
FIG. 14. Single-cell RNA gene expression heatmap of different samples. Clustered by cell types using Loupe Browser.

On day 159 of differentiation, RtOgs in both groups (FIG. 9) demonstrated a distinct and compact photoreceptor outer nuclear layer (ONL), marked by the immunoreactivity for neural retina-specific leucine zipper protein (NRL) (FIGS. 9A, D) and OTX2 (FIGS. 9C, F). When comparing FIG. 9A and FIG. 9D, the bioreactor group had a thicker ONL. However, this difference is not significant, as shown in the NRL+ cell counting result in FIG. 911. Photoreceptor outer segment structures were shown on the apical aspect, marked by rhodopsin (RHO). The basal aspects were composed of retinal progenitor cells (CHX10) and amacrine cells (CAL2) (FIGS. 9C, F). Rod bipolar cells immunoreactive for protein kinase (PKC)-α formed the inner nuclear layer (INL) (FIGS. 9B, E). The expression of synaptophysin (SYP) indicated synaptogenesis through the inner plexiform layer (IPL) to ONL (FIGS. 9B, D). High-resolution SEM images showed that RtOgs in both static and bioreactor groups differentiated matured photoreceptor cells with inner segment (IS), connecting cilium (CC) and outer segment (OS) (FIG. 9G, I). More electron microscopic images are shown in FIG. 13. Cell counting from the immunohistology staining sections showed no significant difference between static and bioreactor groups (FIG. 9H).

III. DISCUSSION

First, a hybrid bioreactor design was developed that incorporated both micro- and millifluidic components. This design was made possible with the novel fabrication method based on SLA 3D printers to create a mold incorporating micro-, milli- and even macroscopic features (FIGS. 3A-D). 3D printing also enabled rapid prototyping bioreactor designs to iteratively optimize the design. This additive manufacturing offers cost savings and reduced facility requirement compared with traditional microfabrication methods and serves as an attractive alternative to manufacturing bioreactors[69].

Computer simulation was used to first demonstrate that each millifluidic culture chamber could be supplied with media from a microfluidic channel. Flow velocity inside culture chambers was evaluated with no active flow being found (FIG. 5C), which satisfied the design goals to minimize turbulence and shear stresses on retinal organoids by eliminating fluidic movement in the culture chamber.

Channel geometry was further optimized relative to the culture chambers and flow rate of media through the bioreactor. The endpoint for determining success in each design iteration was comparing uniformity of media composition in each culture chamber. Both COMSOL simulations in silico (FIG. 5) as well as dye tests in vitro (FIG. 6) were performed In silico simulations demonstrated that narrow microfluidic channels (500 μm wide×200 μm tall) allowed greater mass transfer than wider microfluidic channels (1 mm wide×200 μm tall). It was also observed in silico that high flow rate (250 vs 600 μL/hr) also improved mass transfer into culture chambers (FIG. 5B). In vitro dye tests to confirm in silico modeling predictably revealed that bioreactor designs with all culture chambers arranged on the same side of the microfluidic channel suffered from diffusion from a single side of the channels laminar flow. This resulted in the first chamber in each row of the microfluidic series to have the highest mass transfer of fresh media, while the last chamber had the lowest (FIG. 6A).

To overcome this limitation, a bioreactor with serpentine microfluidic flow line and culture chambers on alternating sides of the microfluidic flow line was designed. These designs were simulated in silico to reveal improved concentration uniformity in each culture chamber compared with straight channel designs. In vitro dye testing confirmed that media concentration variability between all wells was improved by the serpentine design (FIG. 6B).

Finally, mixers were introduced in the flow channel to determine if mixing would improve culture chamber concentration uniformity. In silico simulation demonstrated improved chamber concentration uniformity over the serpentine channel design (FIG. 6A). In vitro dye testing demonstrated a marginal improvement when the mixer was included than when it was not. A decision based on practical implementation was made to exclude the mixer because of the higher probability of trapping bubbles in the mixer elements as well as the mixer having tapered features that exceeded the resolution of the 3D printers employed.

A second major requirement for the design was to enable imaging of retinal organoids maintained in perfused culture. The bioreactor chip design included glass cover slips to seal the microfluidic circuit. Glass cover slips are thinner than microscope slides and, therefore, suitable for both multiphoton imaging and conventional fluorescence microscopy. Multiphoton imaging relies upon optimally efficient photon capture, and thicker glass slide reduces captured photons below threshold of practical imaging.

A third major requirement for the design is to facilitate RtOgs' long-term maintenance in automated culture. Organoids in three different differentiation stages (41, 88 and 128 days) that were either placed in the bioreactor for 31 to 37 days or remained in conventional plate culture were compared. Non-invasive functional imaging of metabolism and oxidative stress, sustained development of photoreceptors on the organoids outer layer, and terminal gene and immunohistology analysis of RtOg tissue were endpoints for comparing culture conditions.

Phase contrast microscopy revealed that RtOgs maintained in conventional culture and bioreactors developed a comparable semi-translucent outer layer on day 128 and outer segment-like structures on day 158 of differentiation (FIG. 5C-F).

FLIM for live RtOg characterization[71] were previously used. The hypothesis in this study was that chip cultured RtOgs would experience less oxidative stress caused by reactive oxygen species (ROS), and the sufficient nutrients supply would benefit RtOgs survival and maturation. On day 38 of differentiation the f/b ratio was the highest (FIG. 6N) since the RtOgs were just cut from the Matrigel. The value decreased over time, which suggested that RtOgs were more differentiated from a stem cell state (glycolytic)[72,73]. Bioreactor cultured RtOgs at all timepoints presented similar f/b NADH ratio as those in static culture, indicating similar differentiated state[74]

Furthermore, organoids in the bioreactor demonstrated significant lower LLS levels suggesting that they experienced less oxidative stress than organoids maintained in conventional tissue culture while imaging (FIG. 6O). A significant increase of LLS ratio was shown over time (FIG. 6O), which suggested a higher demand for oxygen and a trend to a hypoxic environment as RtOgs became more mature.

Differences between different stem cell lines were further confirmed by qPCR. For the selected retinal genes, there was no significant difference between RtOgs maintained in conventional culture or the bioreactor in both CRX-GFP and CSC-14 hESC lines (FIGS. 7F-G). However, both static and bioreactor cultured RtOgs on day 105 and 124 showed low mature photoreceptor gene expression, which was expected, as RtOgs typically do not reach full maturity until day 150 of differentiation. Immunohistology and scRNA seq analysis of organoids maintained in the bioreactor or in conventional culture showed cellular and structural similarities. Finally, outer segment-like structures were observed through high resolution SEM imaging in day 159 organoids in both culture conditions (FIGS. 9G, I).

IV. CONCLUSION

As set forth above, a bioreactor is designed and optimized for long term RtOg culture in a low shear stress environment that was also compatible with multimodal imaging. It was found that higher flow rate through narrower channel with culture chambers on alternating sides of the perfusion channel enabled optimal and practical concentration uniformity between culture chambers. RtOgs culture on a shear stress-free micro-millifluidic bioreactor for 1 month were subsequently achieved. Key similarities and differences between RtOgs maintained in either static culture or the bioreactor were identified. It was found that: 1) bioreactor cultured RtOgs developed cell types and morphology comparable to static cultured ones and exhibited similar retinal genes expression levels; 2) the outer surface region of bioreactor cultured RtOgs had comparable free/bound NADH ratio and overall lower long lifetime species (LLS) ratio than static culture RtOgs during imaging. Therefore, the micro-millifluidic bioreactor has demonstrated its potential to sustain RtOgs of comparable quality to those maintained in static culture, while achieving this goal with reduced labor and a sheer stress-free system.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Trapani, A. Puppo and A. Auricchio, *Progress in retinal and eye research*, 2014, 43, 108-128.
2. M. F. Dias, K. Joo, J. A. Kemp, S. L. Fialho, A. da Silva Cunha Jr, S. J. Woo and Y. J. Kwon, *Progress in retinal and eye research*, 2018, 63, 107-131.
3. M. J. Seiler, R. B. Aramant and S. L. Ball, *Vision Res*, 1999, 39, 2589-2596.
4. G. Woch, R. B. Aramant, M. J. Seiler, B. T. Sagdullaev and M. A. McCall, *Invest Ophthalmol Vis Sci*, 2001, 42, 1669-1676.
5. B. T. Sagdullaev, R. B. Aramant, M. J. Seiler, G. Woch and M. A. McCall, *Invest Ophthalmol Vis Sci*, 2003, 44, 1686-1695.
6. B. B. Thomas, M. J. Seiler, S. R. Sadda and R. B. Aramant, *Exp Eye Res*, 2004, 79, 29-39.
7. P. B. Yang, M. J. Seiler, R. B. Aramant, F. Yan, M. J. Mahoney, L. M. Kitzes and H. S. Keirstead, *Exp Eye Res*, 2010, 91, 727-738.
8. M. J. Seiler, R. E. Lin, B. T. McLelland, A. Mathur, B. Lin, J. Sigman, A. T. De Guzman, L. M. Kitzes, R. B. Aramant and B. B. Thomas, *Invest Ophthalmol Vis Sci*, 2017, 58, 614-630.
9. B. B. Thomas, R. B. Aramant, S. R. Sadda and M. J. Seiler, in *Retinal Degenerative Diseases*, eds. J. G. Hollyfield, R. E. Anderson and M. M. LaVail, Springer, New York, NY, 2006, pp. 367-376.
10. R. B. Aramant and M. J. Seiler, *Prog Retin Eye Res*, 2004, 23, 475-494.
11. M. J. Seiler, R. B. Aramant and H. S. Keirstead, *Optics and Photonics News*, 2008, 19, 37-47.
12. M. J. Seiler and R. B. Aramant, *Prog Retin Eye Res*, 2012, 31, 661-687.
13. N. D. Radtke, R. B. Aramant, H. M. Petty, P. T. Green, D. J. Pidwell and M. J. Seiler, *Am J Ophthalmol*, 2008, 146, 172-182.
14. B. A. Tucker, I. H. Park, S. D. Qi, H. J. Klassen, C. Jiang, J. Yao, S. Redenti, G. Q. Daley and M. J. Young, *PLoS ONE*, 2011, 6, e18992.
15. R. A. Pearson, A. C. Barber, M. Rizzi, C. Hippert, T. Xue, E. L. West, Y. Duran, A. J. Smith, J. Z. Chuang, S. A. Azam, U. F. Luhmann, A. Benucci, C. H. Sung, J. W. Bainbridge, M. Carandini, K. W. Yau, J. C. Sowden and R. R. Ali, *Nature*, 2012, 485, 99-103.
16. M. S. Singh, P. Charbel Issa, R. Butler, C. Martin, D. M. Lipinski, S. Sekaran, A. R. Barnard and R. E. MacLaren, *Proc Natl Acad Sci USA*, 2013, 110, 1101-1106.
17. D. A. Lamba, J. Gust and T. A. Reh, *Cell Stem Cell*, 2009, 4, 73-79.

18. R. E. MacLaren, R. A. Pearson, A. MacNeil, R. H. Douglas, T. E. Salt, M. Akimoto, A. Swaroop, J. C. Sowden and R. R. Ali, *Nature,* 2006, 444, 203-207.
19. F. C. Mansergh, R. Vawda, S. Millington-Ward, P. F. Kenna, J. Haas, C. Gallagher, J. H. Wilson, P. Humphries, M. Ader and G. J. Farrar, *Exp Eye Res,* 2010, 91, 500-512.
20. J. A. Thomson, J. Itskovitz-Eldor, S. S. Shapiro, M. A. Waknitz, J. J. Swiergiel, V. S. Marshall and J. M. Jones, *science,* 1998, 282, 1145-1147.
21. K. Takahashi, K. Tanabe, M. Ohnuki, M. Narita, T. Ichisaka, K. Tomoda and S. Yamanaka, *Cell,* 2007, 131, 861-872.
22. C. M. Fligor, K. B. Langer, A. Sridhar, Y. Ren, P. K. Shields, M. C. Edler, S. K. Ohlemacher, V. M. Sluch, D. J. Zack and C. Zhang, *Scientific reports,* 2018, 8, 14520.
23. K. Wahlin, J. Maruotti, S. Sripathi, J. Ball, J. Angueyra, C. Kim, R. Grebe, W. Li, B. Jones and D. Zack, *Journal,* 2017.
24. T. Nakano, S. Ando, N. Takata, M. Kawada, K. Muguruma, K. Sekiguchi, K. Saito, S. Yonemura, M. Eiraku and Y. Sasai, *Cell Stem Cell,* 2012, 10, 771-785.
25. B. T. McLelland, B. Lin, A. Mathur, R. B. Aramant, B. B. Thomas, G. Nistor, H. S. Keirstead and M. J. Seiler, *Investigative ophthalmology & visual science,* 2018, 59, 2586-2603.
26. J. Assawachananont, M. Mandai, S. Okamoto, C. Yamada, M. Eiraku, S. Yonemura, Y. Sasai and M. Takahashi, *Stem cell reports,* 2014, 2, 662-674.
27. H. Shirai, M. Mandai, K. Matsushita, A. Kuwahara, S. Yonemura, T. Nakano, J. Assawachananont, T. Kimura, K. Saito and H. Terasaki, *Proceedings of the National Academy of Sciences,* 2016, 113, E81-E90.
28. S. Llonch, M. Carido and M. Ader, *Dev Biol,* 2018, 433, 132-143.
29. C. B. Mellough, J. Collin, R. Queen, G. Hilgen, B. Dorgau, D. Zerti, M. Felemban, K. White, E. Sernagor and M. Lako, *Stem cells translational medicine,* 2019, 8, 694-706.
30. Z. Ao, H. Cai, D. J. Havert, Z. Wu, Z. Gong, J. M. Beggs, K. Mackie and F. Guo, *Anal Chem,* 2020, 92, 4630-4638.
31. E. Berger, C. Magliaro, N. Paczia, A. S. Monzel, P. Antony, C. L. Linster, S. Bolognin, A. Ahluwalia and J. C. Schwamborn, *Lab Chip,* 2018, 18, 3172-3183.
32. M. E. Boutin, C. Hampton, R. Quinn, M. Ferrer and M. J. Song, *Adv Exp Med Biol,* 2019, 1186, 171-193.
33. T. DiStefano, H. Y. Chen, C. Panebianco, K. D. Kaya, M. J. Brooks, L. Gieser, N. Y. Morgan, T. Pohida and A. Swaroop, *Stem cell reports,* 2018, 10, 300-313.
34. L. Goto-Silva, N. M. E. Ayad, I. L. Herzog, N. P. Silva, B. Lamien, H. R. B. Orlande, A. da Costa Souza, S. Ribeiro, M. Martins, G. B. Domont, M. Junqueira, F. Tovar-Moll and S. K. Rehen, *BMC Dev Biol,* 2019, 19, 3.
35. P. Ovando-Roche, E. L. West, M. J. Branch, R. D. Sampson, M. Fernando, P. Munro, A. Georgiadis, M. Rizzi, M. Kloc, A. Naeem, J. Ribeiro, A. J. Smith, A. Gonzalez-Cordero and R. R. Ali, *Stem Cell Res Ther,* 2018, 9, 156.
36. M. A. Phelan, P. I. Lelkes and A. Swaroop, *Stem Cell Investig,* 2018, 5, 33.
37. A. Artero Castro, F. J. Rodriguez Jimenez, P. Jendelova and S. Erceg, *Stem Cells,* 2019, 37, 1496-1504.
38. D. Smith, et al., 2014.
39. E. Berger, C. Magliaro, N. Paczia, A. S. Monzel, P. Antony, C. L. Linster, S. Bolognin, A. Ahluwalia and J. C. Schwamborn, *Lab on a Chip,* 2018, 18, 3172-3183.
40. B. Sidar, B. R. Jenkins, S. Huang, J. R. Spence, S. T. Walk and J. N. Wincing, *Lab Chip,* 2019, 19, 3552-3562.
41. M. J. Beauchamp, G. P. Nordin and A. T. Woolley, *Anal Bioanal Chem,* 2017, 409, 4311-4319.
42. D. Qin, Y. Xia and G. M. Whitesides, *Nature protocols,* 2010, 5, 491-502.
43. J. Collin, C. B. Mellough, B. Dorgau, S. Przyborski, I. Moreno-Gimeno and M. Lako, *Stem Cells,* 2016, 34, 311-321.
44. J. Collin, R. Queen, D. Zerti, B. Dorgau, R. Hussain, J. Coxhead, S. Cockell and M. Lako, *Stem Cells,* 2019, 37, 593-598.
45. J. Collin, D. Zerti, R. Queen, T. Santos-Ferreira, R. Bauer, J. Coxhead, R. Hussain, D. Steel, C. Mellough and M. Ader, *Stem Cells,* 2019, 37, 609-622.
46. X. Zhong, C. Gutierrez, T. Xue, C. Hampton, M. N. Vergara, L.-H. Cao, A. Peters, T. S. Park, E. T. Zambidis and J. S. Meyer, *Nature communications,* 2014, 5, 4047.
47. M. A. Digman, V. R. Caiolfa, M. Zamai and E. Gratton, *Biophys J,* 2008, 94, L14-16.
48. S. Ranjit‡, L. Malacridal, M. Stakic and E. Gratton.
49. C. Stringari, J. L. Nourse, L. A. Flanagan and E. Gratton, *PloS one,* 2012, 7, e48014.
50. R. Datta, A. Alfonso-Garcia, R. Cinco and E. Gratton, *Sci Rep,* 2015, 5, 9848.
51. C.-C. Hong, J.-W. Choi and C. H. Ahm, *Lab on a Chip,* 2004, 4, 109-113.
52. A. Sridhar, A. Hoshino, C. R. Finkbeiner, A. Chitsazan, L. Dai, A. K. Haugan, K. M. Eschenbacher, D. L. Jackson, C. Trapnell and 0. Bermingham-McDonogh, *Cell reports,* 2020, 30, 1644-1659. e1644.
53. K. Shekhar, S. W. Lapan, I. E. Whitney, N. M. Tran, E. Z. Macosko, M. Kowalczyk, X. Adiconis, J. Z. Levin, J. Nemesh and M. Goldman, *Cell,* 2016, 166, 1308-1323. e1330.
54. J. E. Niven and S. B. Laughlin, *The Journal of experimental biology,* 2008, 211, 1792-1804.
55. R. P. Wolfe and T. Ahsan, *Biotechnology and bioengineering,* 2013, 110, 1231-1242.
56. S. Regmi, A. Fu and K. Q. Luo, *Scientific Reports,* 2017, 7, 39975.
57. J. A. Frangos, L. V. McIntire and S. G. Eskin, *Biotechnology and bioengineering,* 1988, 32, 1053-1060.
58. P. Ovando-Roche, E. L. West, M. J. Branch, R. D. Sampson, M. Fernando, P. Munro, A. Georgiadis, M. Rizzi, M. Kloc, A. Naeem, J. Ribeiro, A. J. Smith, A. Gonzalez-Cordero and R. R. Ali, *Stem Cell Research & Therapy,* 2018, 9, 156.
59. A. Schwartz, Transactions of the American Ophthalmological Society, 1972, 70, 178.
60. Y. C. Smith, Grande, K. K., Rasmussen, S. B., & O'Brien, A. D., 2006.
61. A. J. Carterson, Höner zu Bentrup, K., Ott, C. M., Clarke, M. S., Pierson, D. L., Vanderburg, C. R., Buchanan, K. L., Nickerson, C. A., Schurr, M. J., *Infection and Immunity,* 2005, 73, 1129-1140.
62. R. Salemo-Goncalves, A. Fasano and M. B. Sztein, *J Vis Exp,* 2016, DOI: 10.3791/54148.
63. B. E. Hjelm, A. N. Berta, C. A. Nickerson, C. J. Arntzen and M. M. Herbst-Kralovetz, *Biol Reprod,* 2010, 82, 617-627.
64. K. A. Homan, N. Gupta, K. T. Kroll, D. B. Kolesky, M. Skylar-Scott, T. Miyoshi, D. Mau, M. T. Valerius, T. Ferrante, J. V. Bonventre, J. A. Lewis and R. Morizane, *Nat Methods,* 2019, 16, 255-262.
65. S. D. Ramachandran, K. Schirmer, B. Munst, S. Heinz, S. Ghafoory, S. Wolff, K. Simon-Keller, A. Marx, C. I. Oie, M. P. Ebert, H. Walles, J. Braspenning and K. Breitkopf-Heinlein, *PLoS One,* 2015, 10, e0139345.

66. M. Kasendra, A. Tovaglieri, A. Sontheimer-Phelps, S. Jalili-Firoozinezhad, A. Bein, A. Chalkiadaki, W. Scholl, C. Zhang, H. Rickner, C. A. Richmond, H. Li, D. T. Breault and D. E. Ingber, *Sci Rep,* 2018, 8, 2871.
67. Y. S. Zhang, J. Aleman, S. R. Shin, T. Kilic, D. Kim, S. A. Mousavi Shaegh, S. Massa, R. Riahi, S. Chae, N. Hu, H. Avci, W. Zhang, A. Silvestri, A. Sanati Nezhad, A. Manbohi, F. De Ferrari, A. Polini, G. Calzone, N. Shaikh, P. Alerasool, E. Budina, J. Kang, N. Bhise, J. Ribas, A. Pourmand, A. Skardal, T. Shupe, C. E. Bishop, M. R. Dokmeci, A. Atala and A. Khademhosseini, *Proc Natl Acad Sci USA,* 2017, 114, E2293-E2302.
68. G. Mattei, Giusti, Serena, Ahluwalia, Arti, 2014, 2, 548-569.
69. N. P. Macdonald, J. M. Cabot, P. Smejkal, R. M. Guijt, B. Paull and M. C. Breadmore, *Analytical Chemistry,* 2017, 89, 3858-3866.
70. K. P. Archberger, C.; Haderspeck, J.; Bolz, S.; Rogal, J.; Chuchuy, J.; Nikolova, M.; Cora, V.; Antowiak, L.; Haq, W.; Shen, N.; Schenke-Layland, K.; Ueffing, M.; Liebau, S.; Loskill, P., *eLife* 2019, DOI: 10.7554/eLife.46188.
71. A. W. Browne, C. Arnesano, N. Harutyunyan, T. Khuu, J. C. Martinez, H. A. Pollack, D. S. Koos, T. C. Lee, S. E. Fraser, R. A. Moats, J. G. Aparicio and D. Cobrinik, *Invest Ophthalmol Vis Sci,* 2017, 58, 3311-3318.
72. C. Stringari, R. A. Edwards, K. T. Pate, M. L. Waterman, P. J. Donovan and E. Gratton, *Scientific reports,* 2012, 2, 1-9.
73. B. K. Wright, L. M. Andrews, J. Markham, M. R. Jones, C. Stringari, M. A. Digman and E. Gratton, *Biophysical journal,* 2012, 103, L7-L9.
74. R. Datta, C. Heylman, S. C. George and E. Gratton, *Biomedical optics express,* 2016, 7, 1690-1701.

What is claimed is:

1. A bioreactor device comprising:
a solid substrate having a first face and a second face, the solid substrate at least partially defining a perfusion channel, a plurality of chambers, a fluidic inlet, and a fluidic outlet;
a first sheet disposed over the first face; and
a second sheet disposed over the second face, wherein the combination of the solid substrate, the first sheet, and the second sheet defining the perfusion channel and each chamber of the plurality of chambers, the plurality of chambers being arranged in rows of chambers, the perfusion channel extending from the fluidic inlet and the fluidic outlet with a serpentine path that weaves through each row of chambers such that adjacent chambers are positioned at opposite sides of the perfusion channel, each chamber being in fluid communication with the perfusion channel, wherein each chamber has an associated connecting channel that provides fluid communication between each chamber and the perfusion channel, each associated connecting channel defining a distance from the perfusion channel that eliminates fluidic movement in each chamber and reduces shear stress.

2. The bioreactor device of claim 1 further comprising a mixer disposed between adjacent chambers.

3. The bioreactor device of claim 2 wherein the mixer defines a tortuous path for fluid flowing therethrough.

4. The bioreactor device of claim 1 wherein the first sheet and the second sheet are each independently transparent to wavelengths of light for performing spectral analysis or imaging or microscopy.

5. The bioreactor device of claim 1 wherein the first sheet and the second sheet are each independently transparent to wavelengths of light for multiphoton imaging.

6. The bioreactor device of claim 1 wherein the first sheet and the second sheet are each independently transparent to wavelengths of light for fluorescence microscopy.

7. The bioreactor device of claim 1 wherein the solid substrate is composed of a moldable polymer.

8. The bioreactor device of claim 7 wherein the moldable polymer is polydimethylsiloxane.

9. The bioreactor device of claim 1 further comprising a media reservoir in fluid communication with the fluid inlet.

10. The bioreactor device of claim 7 further comprising a pumping device for drawing fluid through the perfusion channel.

11. The bioreactor device of claim 1 wherein the perfusion channel has a height from 150-300 μm and each chamber has a height from 2-7 mm.

12. The bioreactor device of claim 1 wherein each chamber has an associated connecting channel that provides fluid communication between each chamber and the perfusion channel.

13. The bioreactor device of claim 12 wherein each associated connecting channel defines a distance from the perfusion channel each associated chamber that eliminates fluidic movement in each chamber, reducing shear stress to allow for long-term culturing of organoids.

14. The bioreactor device of claim 1 wherein the solid substrate is fabricated by
3D printing a mold template for the solid substrate, the mold template having open template regions corresponding to solid substrate regions in the solid substrate and sold template regions corresponding to open substrate regions in the solid substrate;
pouring a liquid polymer precursor over the mold template such that the open template regions are filled with liquid polymer precursor;
curing the liquid polymer precursor in the mold template; and
removing the solid substrate from the mold template.

15. A bioreactor device comprising:
a solid substrate having a first face and a second face, the solid substrate at least partially defining a perfusion channel, a plurality of chambers, a fluidic inlet, and a fluidic outlet;
a first sheet disposed over the first face; and
a second sheet disposed over the second face, wherein the combination of the solid substrate, the first sheet and the second sheet defining the perfusion channel and each chamber of the plurality of chambers, the plurality of chambers being arranged in rows of chambers, the perfusion channel extending from the fluidic inlet and the fluidic outlet with a serpentine path that weaves through each row of chambers such that adjacent chambers are positioned at opposite sides of the perfusion channel, wherein each chamber has an associated connecting channel that provides fluid communication between each chamber and the perfusion channel, each associated connecting channel defining a distance from the perfusion channel that eliminates fluidic movement in each chamber and reduces shear stress; and
a plurality of mixers positioned in the perfusion channel wherein at least one mixer is disposed between adjacent chambers.

* * * * *